(12) United States Patent
De et al.

(10) Patent No.: US 12,002,465 B2
(45) Date of Patent: *Jun. 4, 2024

(54) SYSTEMS AND METHODS FOR MANAGING VOICE ENVIRONMENTS AND VOICE ROUTINES

(71) Applicant: Voice Care Tech Holdings LLC, Boston, MA (US)

(72) Inventors: Nirmalya K. De, Sunnyvale, CA (US); Alan R. Bugos, Westford, MA (US); Dale M. Smith, Marblehead, MA (US); Stuart R. Patterson, Hull, MA (US); Jonathan E. Gordon, Bearsville, NY (US)

(73) Assignee: Voice Care Tech Holdings LLC, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/875,897

(22) Filed: Jul. 28, 2022

(65) Prior Publication Data

US 2023/0066964 A1 Mar. 2, 2023

Related U.S. Application Data

(63) Continuation of application No. 17/385,471, filed on Jul. 26, 2021, now Pat. No. 11,404,062.

(51) Int. Cl.
*G10L 15/22* (2006.01)
*G10L 15/30* (2013.01)
(Continued)

(52) U.S. Cl.
CPC .............. *G10L 15/22* (2013.01); *G10L 15/30* (2013.01); *G06F 3/0482* (2013.01); *G06F 3/167* (2013.01);
(Continued)

(58) Field of Classification Search
CPC ... G10L 15/22; G10L 15/30; G10L 2015/223; G06F 3/0482; G06F 3/167; G06F 3/165; G16H 40/63; G16H 40/20
See application file for complete search history.

(56) References Cited

U.S. PATENT DOCUMENTS 5,086,391 A 2/1992 Chambers
5,612,869 A 3/1997 Letzt
(Continued)

FOREIGN PATENT DOCUMENTS

WO WO 2016/097368 A1 6/2016

OTHER PUBLICATIONS

International Search Report and Written Opinion dated Aug. 9, 2018, in connection with International Application No. PCT/US2018/031783.

(Continued)

*Primary Examiner* — Abul K Azad
(74) *Attorney, Agent, or Firm* — Wolf, Greenfield & Sacks, P.C.

(57) ABSTRACT

Provided is a voice assistance system with proactive routines that couples a remote server and respective user voice interactive devices to deliver a complete experience to the end user of the device. The user devices can be managed by groups and/or associated entities who manage voice services for their users. For example, the entities can provide preconfigured voice routines that perform actions on behalf of their users. The voice assistance system can also allow users to customize these routines to improve day to day operation. In addition, external services and/or providers can be linked to the system and allowed to define routines that have external system dependencies. Avoiding and managing conflicts in this environment becomes quite challenging. Some approaches use execution queues and priority, others invoke (Continued)

time slices and limitations on assignment of routines to time slices to resolve these issues, among other examples.

20 Claims, 20 Drawing Sheets

(51) Int. Cl.
*G06F 3/0482* (2013.01)
*G06F 3/16* (2006.01)
*G16H 40/63* (2018.01)

(52) U.S. Cl.
CPC ........ *G10L 2015/223* (2013.01); *G16H 40/63* (2018.01)

(56) References Cited

U.S. PATENT DOCUMENTS

| | | | |
|---|---|---|---|
| 5,625,864 | A | 4/1997 | Budow |
| 6,091,362 | A | 7/2000 | Stilp et al. |
| 6,335,927 | B1 | 1/2002 | Elliot et al. |
| 7,412,260 | B2 | 8/2008 | Gailey et al. |
| 7,827,040 | B2 | 11/2010 | Brown |
| 8,311,863 | B1 | 11/2012 | Kemp |
| 9,363,656 | B1 | 6/2016 | George et al. |
| 9,503,873 | B1 | 11/2016 | Yadav |
| 9,715,814 | B2 | 7/2017 | Sattari |
| 9,786,148 | B2 | 10/2017 | Sundaram |
| 9,852,599 | B1 | 12/2017 | Slavin et al. |
| 9,918,212 | B1 | 3/2018 | Immendorf et al. |
| 10,258,295 | B2 | 4/2019 | Fountaine |
| 10,311,707 | B2 | 6/2019 | Halverson |
| 10,412,206 | B1 | 9/2019 | Liang et al. |
| 10,516,622 | B2 | 12/2019 | Liu |
| 10,572,107 | B1 | 2/2020 | Beebe et al. |
| 10,658,074 | B1 | 5/2020 | Sorkey et al. |
| 10,722,185 | B2 | 7/2020 | Fountaine |
| 11,020,064 | B2 | 6/2021 | Fountaine |
| 11,404,062 | B1 * | 8/2022 | De ........................... G06F 3/165 |
| 2001/0054085 | A1 | 12/2001 | Kurganov |
| 2002/0026266 | A1 | 2/2002 | Montague |
| 2002/0150227 | A1 | 10/2002 | Abraham |
| 2003/0052787 | A1 | 3/2003 | Zerhusen et al. |
| 2004/0143602 | A1 | 7/2004 | Ruiz et al. |
| 2005/0075542 | A1 | 4/2005 | Goldreich |
| 2005/0240571 | A1 | 10/2005 | Haigh et al. |
| 2005/0288721 | A1 | 12/2005 | Girouard et al. |
| 2006/0049936 | A1 | 3/2006 | Collins, Jr. et al. |
| 2006/0053009 | A1 | 3/2006 | Jeong et al. |
| 2006/0143050 | A1 | 6/2006 | Dean |
| 2006/0184369 | A1 | 8/2006 | Levonas |
| 2006/0288225 | A1 | 12/2006 | Jung et al. |
| 2007/0037605 | A1 | 2/2007 | Logan |
| 2007/0066276 | A1 | 3/2007 | Kuz et al. |
| 2007/0106510 | A1 | 5/2007 | Hsing et al. |
| 2007/0189128 | A1 | 8/2007 | Chung |
| 2007/0253021 | A1 | 11/2007 | Mehta et al. |
| 2007/0255599 | A1 | 11/2007 | Henry |
| 2008/0089491 | A1 | 4/2008 | Kortum et al. |
| 2008/0165286 | A1 | 7/2008 | Oh et al. |
| 2008/0247519 | A1 | 10/2008 | Abella et al. |
| 2008/0294462 | A1 | 11/2008 | Nuhaan et al. |
| 2009/0243833 | A1 | 10/2009 | Huang et al. |
| 2009/0259728 | A1 | 10/2009 | Berisford et al. |
| 2010/0015585 | A1 | 1/2010 | Baker |
| 2010/0131280 | A1 | 5/2010 | Bogineni |
| 2010/0269049 | A1 | 10/2010 | Fearin |
| 2010/0295684 | A1 | 11/2010 | Hsieh |
| 2011/0059748 | A1 | 3/2011 | Taylor et al. |
| 2011/0123971 | A1 | 5/2011 | Berkowitz |
| 2011/0282671 | A1 | 11/2011 | Dicks et al. |
| 2011/0301440 | A1 | 12/2011 | Riley et al. |
| 2012/0087482 | A1 | 4/2012 | Alexander, Sr. |
| 2012/0166322 | A1 | 6/2012 | Simon |
| 2012/0196571 | A1 | 8/2012 | Grkov et al. |
| 2013/0077536 | A1 | 3/2013 | Piett et al. |
| 2013/0097682 | A1 | 4/2013 | Zeljkovic et al. |
| 2013/0147899 | A1 | 6/2013 | Labhard |
| 2013/0149987 | A1 | 6/2013 | Cheng et al. |
| 2013/0150686 | A1 | 6/2013 | Fronterhouse et al. |
| 2013/0267795 | A1 | 10/2013 | Cosentino et al. |
| 2014/0019157 | A1 | 1/2014 | Nudd et al. |
| 2014/0073880 | A1 | 3/2014 | Boucher et al. |
| 2014/0168453 | A1 | 6/2014 | Shoemake et al. |
| 2014/0214426 | A1 | 7/2014 | Kanevsky et al. |
| 2014/0259017 | A1 | 9/2014 | Murray et al. |
| 2014/0351411 | A1 | 11/2014 | Woods et al. |
| 2014/0379344 | A1 | 12/2014 | Smith et al. |
| 2015/0002292 | A1 | 1/2015 | Cavalcanti et al. |
| 2015/0094830 | A1 | 4/2015 | Lipoma et al. |
| 2015/0116107 | A1 | 4/2015 | Fadell et al. |
| 2015/0162006 | A1 | 6/2015 | Kummer |
| 2015/0185752 | A1 | 7/2015 | Bard et al. |
| 2015/0193450 | A1 | 7/2015 | Chung |
| 2015/0206531 | A1 | 7/2015 | Fujisawa et al. |
| 2015/0269827 | A1 | 9/2015 | Hopkins et al. |
| 2015/0295784 | A1 | 10/2015 | Kim et al. |
| 2015/0302766 | A1 | 10/2015 | Oberlander |
| 2015/0373183 | A1 | 12/2015 | Woolsey et al. |
| 2016/0041811 | A1 | 2/2016 | Parundekar et al. |
| 2016/0052391 | A1 | 2/2016 | Walsh et al. |
| 2016/0057595 | A1 | 2/2016 | Ahmed et al. |
| 2016/0066189 | A1 | 3/2016 | Mahaffey et al. |
| 2016/0088455 | A1 | 3/2016 | Bozik et al. |
| 2016/0106627 | A1 | 4/2016 | Geman et al. |
| 2016/0179787 | A1 | 6/2016 | Deleeuw |
| 2016/0232773 | A1 | 8/2016 | Abeyta et al. |
| 2016/0324460 | A1 | 11/2016 | Kusens |
| 2017/0083622 | A1 | 3/2017 | Blanco |
| 2017/0094490 | A1 | 3/2017 | Ryan et al. |
| 2017/0103754 | A1 | 4/2017 | Higbie et al. |
| 2017/0123391 | A1 | 5/2017 | Sinha et al. |
| 2017/0124279 | A1 | 5/2017 | Rothman |
| 2017/0140629 | A1 | 5/2017 | Briggs et al. |
| 2017/0140754 | A1 | 5/2017 | Ichimura |
| 2017/0160813 | A1 | 6/2017 | Divakaran et al. |
| 2017/0186301 | A1 | 6/2017 | Vaddepally et al. |
| 2017/0206899 | A1 | 7/2017 | Bryant et al. |
| 2017/0213191 | A1 | 7/2017 | Pitcher |
| 2017/0221283 | A1 | 8/2017 | Pal et al. |
| 2017/0239432 | A1 | 8/2017 | Delangre et al. |
| 2017/0251347 | A1 | 8/2017 | Mehta et al. |
| 2018/0004909 | A1 | 1/2018 | Cronin et al. |
| 2018/0007201 | A1 | 1/2018 | Kurganov |
| 2018/0047391 | A1 | 2/2018 | Baik et al. |
| 2018/0054506 | A1 | 2/2018 | Hart et al. |
| 2018/0060492 | A1 | 3/2018 | Feng et al. |
| 2018/0060495 | A1 | 3/2018 | Mahapatra et al. |
| 2018/0075219 | A1 | 3/2018 | Klein et al. |
| 2018/0096690 | A1 | 4/2018 | Mixter et al. |
| 2018/0122378 | A1 | 5/2018 | Mixter et al. |
| 2018/0144590 | A1 | 5/2018 | Mixter et al. |
| 2018/0190264 | A1 | 7/2018 | Mixter et al. |
| 2018/0210701 | A1 | 7/2018 | Segal et al. |
| 2018/0217264 | A1 | 8/2018 | Syrjarinne |
| 2018/0226158 | A1 | 8/2018 | Fish et al. |
| 2018/0268337 | A1 * | 9/2018 | Miller ................ G06Q 10/109 |
| 2018/0268346 | A1 | 9/2018 | Cronin et al. |
| 2018/0310159 | A1 | 10/2018 | Katz et al. |
| 2018/0325469 | A1 | 11/2018 | Fountaine |
| 2018/0325470 | A1 | 11/2018 | Fountaine |
| 2019/0132932 | A1 | 5/2019 | Klecha et al. |
| 2019/0163437 | A1 | 5/2019 | Nagasaka |
| 2019/0221225 | A1 | 7/2019 | Bricklin et al. |
| 2019/0228631 | A1 | 7/2019 | Stinson et al. |
| 2019/0233870 | A1 | 8/2019 | Buck et al. |
| 2019/0290129 | A1 | 9/2019 | Hanina |
| 2019/0343456 | A1 | 11/2019 | Kahlert et al. |
| 2019/0364505 | A1 | 11/2019 | Wang et al. |
| 2019/0378518 | A1 | 12/2019 | Jeong et al. |
| 2020/0043502 | A1 | 2/2020 | Ding |
| 2020/0047341 | A1 | 2/2020 | Song et al. |
| 2020/0066254 | A1 | 2/2020 | Hiroe et al. |
| 2020/0114159 | A1 | 4/2020 | Kaib et al. |

(56) References Cited

U.S. PATENT DOCUMENTS

| | | |
|---|---|---|
| 2020/0265699 A1 | 8/2020 | Bango et al. |
| 2020/0286620 A1 | 9/2020 | Fallon et al. |
| 2020/0327989 A1 | 10/2020 | Kuenen et al. |
| 2020/0380980 A1 | 12/2020 | Shum et al. |
| 2021/0038170 A1 | 2/2021 | Fountaine |
| 2021/0077036 A1 | 3/2021 | Fountaine |
| 2021/0104304 A1 | 4/2021 | Davidovics et al. |
| 2021/0142798 A1 | 5/2021 | Pulicharla et al. |
| 2021/0153818 A1 | 5/2021 | Fountaine |
| 2021/0158722 A1 | 5/2021 | Vyas et al. |
| 2021/0196209 A1 | 7/2021 | Fountaine |
| 2023/0070082 A1 | 3/2023 | De et al. |

OTHER PUBLICATIONS

International Preliminary Report on Patentability dated Nov. 21, 2019, in connection with International Application No. PCT/US2018/031783.

\* cited by examiner

| Application (Content) | Capability | Voice Device Feature |
|---|---|---|
| Detailed News/Music/Weather Options | C.R.U.D | Personal |
| ADL Support | Care Plan Connection | Reminders |
| AI-Generated Proactive Routines | AI-Generated Proactive Routines | Reminders |
| Disease-state questions | Care Plan Connection | Clinical |
| Support for PCAs and Home Aide | Care Plan Connection | Clinical |
| Following your care plan | Care Plan Connection | Reminders |
| Authorization (status & decision) | Care Plan Connection | Status |
| Wound Cleaning Routines | Care Plan Connection (temporary) | Clinical |
| Post Discharge Routines | Care Plan Connection (temporary) | Clinical |
| Clinical and Personal Appointments | Care Plan Connection / Member initiated reminders | Reminders |
| Take your medication | Care Plan Connection / Member initiated reminders | Reminders |
| DME/Supplies Order | Care Plan Connection / Vendor Connection | Status |
| DME/Supplies Order Receipt Confirmation | Care Plan Connection / Vendor Connection | Admin Fxn |
| PERS device | Device Development | Clinical |
| Additional Languages (Spanish, Haitian Creole) | Non-English Language Utility | Language |
| Dental Surveys (IVR Replacement) | Surveying | Surveys |
| Rx STARS (IVR Replacement) | Surveying | Surveys |
| Transportation Reminder | Vendor Connection | Reminders |
| Prescription refill reminders | Vendor Connection | Reminders |
| Medication Refill Requests | Vendor Connection | Status |
| Medication Reminders | Vendor Connection | Status |
| Transportation Scheduling / Cancellation | Vendor Connection / Critical Routine | Admin Fxn |

FIG. 4

Routines/Schedules Example

Current Routines/CCA June 2020 (Monday-Friday)

| Organization by Routine or Package Type | | Monday | Tuesday | Wednesday | Thursday | Friday |
|---|---|---|---|---|---|---|
| Starter Pkg | 00, 15, 30, 45 | 8:30 AM: Morning Greeting; 9:00 AM: Today's Weather; 8:00 PM Wellness Check | 8:30 AM: Morning Greeting; 9:00 AM: Today's Weather; 8:00 PM Wellness Check | 8:30 AM: Morning Greeting; 9:00 AM: Today's Weather; 8:00 PM Wellness Check | 8:30 AM: Morning Greeting; 9:00 AM: Today's Weather; 8:00 PM Wellness Check | 8:30 AM: Morning Greeting; 9:00 AM: Today's Weather; 8:00 PM Wellness Check |
| Covid Pkg | 03, 18, 33, 48 | 9:33 AM: Wellness Check; 10:03 AM: COVID Symptoms; 11:03 AM: COVID Hygiene; 7:33 PM Critical Concerns | 9:33 AM: Wellness Check; 11:03 AM COVID Hygiene; 2:33 PM COVID Relaxation; 7:33 PM Critical Concerns | 9:33 AM: Wellness Check; 11:03 AM COVID Hygiene; 3:33 PM COVID Connection; 7:33 PM Critical Concerns | 9:33 AM: Wellness Check; 10:03 AM: COVID Symptoms; 11:03 AM: COVID Hygiene; 7:33 PM Critical Concerns | 9:33 AM: Wellness Check; 11:03 AM COVID Hygiene; 3:33 PM COVID Connection; 7:33 PM Critical Concerns |
| Next Care Plan Pkg | 06, 21, 36, 51 | Up to 4 per hour at any of these time slots | | | | |
| Personalized Routines | 09, 24, 39, 54 | Up to 4 per hour at any of these time slots | | | | |
| Reserved for: Other, Broadcast, User Sat, etc. | 12, 27, 42, 57 | 11:24 AM Customer/User Satisfaction check (bi-monthly) | | | | |

☐ = unused slots for future

☑ Add Routine

☑ Wellness Check-Ins

Designed to check in on and record the response for scheduled care plan items

Sample Check-Ins:

Daily Exercises — 1502
Hydration — 1504
Medication — 1506
Morning Check-In — 1508

[ Create Check-In ]

△ Social Reminders

Reminders of important events to support a healthy & engaged lifestyle

Sample Reminders:

Caregiver Visit Today — 1510
Favorite TV Show — 1512
Religious Service — 1514
Upcoming Birthday — 1514

[ Create Reminder ]

🔊 Streaming Content

Access online content that supports education & entertainment

Sample Content:

Listen to Music — 1516
News Briefing — 1518
Today's Weather — 1520

[ Create Content ]

FIG. 15

SYSTEMS AND METHODS FOR MANAGING VOICE ENVIRONMENTS AND VOICE ROUTINES

RELATED APPLICATIONS

This Application is a Continuation of and claims priority under 35 U.S.C. § 120 to U.S. application Ser. No. 17/385,471, filed Jul. 26, 2021, entitled "SYSTEMS AND METHODS FOR MANAGING VOICE ENVIRONMENTS AND VOICE ROUTINES" which is herein referenced in its entirety.

BACKGROUND

Various systems and devices are configured to provide voice services in almost any known environment where power and internet services are available. The well-known AMAZON ECHO is an example of a reactive voice service device that can be ubiquitous in homes and other spaces. Such devices are configured to react to voice requests and interact with users once activated by such requests.

SUMMARY

The inventors have realized that further functionality and options become available when remote systems are used to design, maintain, administer, and/or trigger voice interaction with users via their voice devices. It is further realized that voice services that are initiated remotely, that is, proactive interactions, represent an area that has not seen wide adoption but has vast application. In one example setting, a care provider can set up or customize routines for a care recipient that are used to trigger functionality at a device located in a caregiving environment.

In such settings, care recipients can participate in conversations with their device that deliver notifications, reminders, and/or instructions on medicine, exercise routines, treatment programs, nutrition, doctor visits, even automatically set up transportation with accompanying reminders, among a host of other options, where the conversations can be triggered proactively and not in response to a user request. These specific functions executed in response to verbal instruction, whether triggered reactively or proactively, can be referred to as a voice routine. Voice routines can include multiple operations and have varying levels of complexity (e.g., order food and resolve nutrition routines), schedule a doctor visit (and schedule transportation with a reminder), etc. Other routines can be executed by or at user devices that include, routines built or triggered by artificial intelligence algorithms, third-party systems, sensor data, user profile matching, etc., and may be collectively referred to as voice routines.

According to various embodiments, the proactive voice requests that are initiated away from the user device can be delivered in various environments beyond caregiving settings and improve not only user interaction with the devices, but also improve execution of any day-to-day task. Such proactive devices open new communication pathways and user customization options through novel and innovative technical implementation needed to ensure proper functioning of the now proactive and reactive voice devices.

According to some aspects, a voice assistance system with proactive routines can couple a remote server or a proactive control server and respective user voice interactive devices to deliver a complete experience to the end user of the device. According to some embodiments, the voice assistance system can also provide a platform to connect remote users who can customize commands (e.g., proactive or reactive) for respective devices, and users with authority to customize proactive routines (e.g., groupings of proactive commands) to improve day to day operation across groups of devices and/or users. For example, routines can be built for an organization and made available to voice interactive devices distributed by or on behalf of the organization. Additionally, administrators can select features for the device and pre-configure voice assistance devices with groups of pre-selected routines, including, for example, proactive routines and/or combine sets of proactive routines to deliver a device that is ready to go out of the box. Moreover, various embodiments provide for a voice interactive device that has sets of baseline or standard functions pre-configured and avoids the tedious and often ignored configuration steps that are required by many conventional approaches. For example, groups of functions and/or associated users can be defined and configured before voice devices are sent out and can be updated based on such groups or associated users once in place. In further embodiments, various devices can be added to respective groups, and the addition of the devices into the groups can trigger updates and configuration of new functionality defined for the group.

In further embodiments, the basic functions associated with the pre-selected groups can also be customized by the user associated with a device. Although preselected routines are configured for a device, the device owner/user (or user with appropriate role for the device (e.g., a caregiver) can further customize operation. In some examples, a user can prevent preconfigured operation from executing or stop further execution. In other examples, the user can customize timing of voice service execution (e.g., initial timing, follow up timing, scheduled timing, day-to-day timing, periodic timing, etc.).

In addition to customizing existing plans or services, users may add their own services and/or create their own routines (e.g., assistance functions) by interacting with their device. According to another aspect, integrating customizations into existing routines presents many challenges. For example, prioritizing of default function versus user created functions can have far reaching effect (e.g., user asked for a custom medication routine which interferes with a default medication plan of an interacting medication). In various embodiments, the voice assistance system is configured to seamlessly integrate customization and automate conflict resolution within default functions and routines and between default functions/routines and any customization requested by the user or other authorized user. According to one embodiment, conflicts in routines can be avoided based on queuing routine execution. For example, the system either remotely or at the respective device can queue sets of routines and operations on a first in first out basis. Other example queuing methodologies can also be implemented. Some embodiments can be configured to evaluate the set of routines for any priority information and order a queue of routines based on an associated priority. Some other embodiments can employ execution windows and execution timing parameters to limit assignment of routines to specific times and/or to avoid overlapping execution.

According to one aspect, a voice assistance system for managing voice routine execution in a user environment is provided. The system comprises at least one processor operatively connected to a memory; at least one server system; a plurality of voice devices, the plurality of voice devices comprising at least a speaker for communicating voice commands and a microphone for receiving voice input, wherein the plurality of voice devices are configured to enable assistance actions for respective users of the voice devices based on execution of voice routines; wherein the at least one processor configured to define associations between a plurality of users and at least some the plurality of voice devices, wherein the plurality of users are associated with an entity providing membership for the plurality of users; configure a plurality of voice routines linked to the associated entity, wherein the plurality of voice routines includes default routines, entity specific routines, and user-based routines, wherein the voice routines include at least a plurality of proactive routines configured to be initiated by the system for execution at a remote voice device; configure a plurality of voice devices with at least a plurality of routines based on selection in a user interface, wherein selection in the user interface includes selection options for selection of individual routines and options for selection of grouped routines, wherein the system is further configured to establish a default schedule for execution of the selected routines responsive to selection in the user interface or further configure to accept specification of a timing for the selected routines in the user interface; and configure the plurality of devices to execute any selection routine based on an associated prioritization; and accept customization of defined routines that change execution parameters for execution at respective ones of the plurality of voice devices.

According to one embodiment, the associated entity is a care service provider, and the plurality of users are care recipients, and the system further comprises an online caregiver portal configured to authenticate caregiver users. According to one embodiment, the system is configured to execute a machine learning model to identify similarity between care recipients and dynamically filter or order a display of the individual routines or grouped routines based on the identified similarity. According to one embodiment, the system is configured to execute a machine learning model to identify individual routines or grouped routines that meet a threshold probability to be assigned to a care recipient, and display the identified routines as recommendations to assign to the care recipient. According to one embodiment, the system is configured to execute a machine learning model to identify customizations to routines for the care recipient, wherein the machine learning model is configured to identify similarity between care recipients and any associated customizations made by similar care recipients. According to one embodiment, the system is configured to display customization options as selectable options in one or more user interfaces shown via the caregiver portal, or generate a verbal request to a care recipient identifying one or more customizations to configure upon receiving a response from the care recipient.

According to one embodiment, the caregiver portal is configured to display user interfaces configured to enable the caregiver users to add individuals from the plurality of users to a care group managed by one or more caregiver users. According to one embodiment, the caregiver portal is configured to display routines and grouped routines available for a care recipient; enable selection of individual or grouped routines in the user interface, and responsive to selection of the individual or group routines, add the respective individual or grouped routines to a user profile. According to one embodiment, the system further comprises routine application programming interfaces (APIs) configured to accept external generation of one or more routines for execution at the plurality of user devices. According to one embodiment, the system is configured to add an external routine to a user profile responsive to the routine API request. According to one embodiment, the system is further configured to store primary instances of the individual routines and grouped routines, wherein alteration of any parameter of the primary instances of the individual routines and grouped routines controls execution of each of the individual routines and grouped routines at the plurality of user devices. According to one embodiment, the system is further configured to store user-based customizations of the individual routines and grouped routines and enable execution of the user-based customizations irrespective of the parameters defined by any primary instance of the individual routines and grouped routines.

According to one embodiment, the system is further configured to accept definition of new routines for execution at respective ones of the plurality of voice devices. According to one embodiment, the system is further configured to generate customization of routines based on at least one or more of the following: previously received responses or interactions with the plurality of devices; a type of response or a frequency of response; a demographic profile or a social profile of a respective user; a medical status or functional status of the user; or a verbal input to a respective user device.

According to one aspect, a computer implemented method for managing voice routine execution in a user environment is provided. The method comprises a plurality of voice devices, the plurality of voice devices comprising at least a speaker for communicating voice commands and a microphone for receiving voice input, wherein the plurality of voice devices are configured to enabling, by at least one processor, assistance actions for respective users of respective voice devices, of a plurality of voice devices, based on execution of voice routines, the enabling including: communicating voice commands via at least one speaker on the respective voice devices; and receiving voice input via a respective microphone; defining, by the at least one processor, associations between a plurality of users and at least some the plurality of voice devices, wherein the plurality of users are associated with an entity providing membership for the plurality of users; configuring, by the at least one processor, a plurality of voice routines linked to the associated entity, wherein the plurality of voice routines includes default routines, entity specific routines, and user-based routines, and wherein the voice routines include at least a plurality of proactive routines configured to be initiated by the system for execution at a remote voice device; configuring, by the at least one processor, a plurality of voice devices with at least a plurality of routines based on selection in a user interface, wherein the configuring includes an act of selecting in the user interface selection options for selection of individual routines and options for selection of grouped routines, establishing, by the at least one processor, a default schedule for execution of the selected routines responsive to the selection in the user interface or accepting, by the at least one processor, specification of a timing for the selected routines in the user interface; and configuring, by the at least one processor, the plurality of devices to execute any selected routine based on an associated prioritization, wherein the configuring includes an act of accepting customization of defined routines that change execution parameters for execution at respective ones of the plurality of voice devices.

According to one embodiment, the associated entity is a care service provider, and the plurality of users are care recipients, and the method further comprises generating an online caregiver portal configured to authenticate caregiver users. According to one embodiment, the method further comprises executing a machine learning model, the executing including an act of identifying similarity between care recipients and dynamically filtering or ordering a display of the individual routines or grouped routines based on the identified similarity. According to one embodiment, the method further comprises an act of executing, by the at least one processor, a machine learning model to identify customizations to routines for the care recipient, wherein the act of executing includes identifying similarity between care recipients and any associated customizations made by similar care recipients.

According to one embodiment, the method further comprises displaying customization options as selectable options in one or more user interfaces shown via the caregiver portal or generating a verbal request to a care recipient identifying one or more customizations to configure upon receiving a response from the care recipient. According to one embodiment, the method further comprises generating customization of routines based on at least one or more of the following: previously received responses or interactions with the plurality of devices; a type of response or a frequency of response; a demographic profile or a social profile of a respective user; a medical status or functional status of the user; or a verbal input to a respective user device.

According to one aspect, a voice assistance system for managing voice routine execution in a user environment is provided. The system comprises at least one processor operatively connected to a memory; at least one server system; a plurality of voice devices, the plurality of voice devices comprising at least a speaker for communicating voice commands and a microphone for receiving voice input, wherein the plurality of voice devices are configured to enable assistance actions for respective users of the voice devices based on execution of voice routines; wherein the at least one processor is configured to manage execution of a plurality of voice routines, the plurality of voice routines having associated execution times or triggers; store primary versions of each voice routine of the plurality of routines; store a user profile for the respective user of the voice device specifying one or more voice routines associated with a respective voice device, wherein the user profile defines the associated execution time or trigger of the one more voice routines in the user profile; identify overlapping execution of a plurality of routines for one or more users; generate an ordering of execution for the plurality of routines for the respective user; and manage execution of the plurality of routines at the respective user's voice device according to the generated ordering.

According to one embodiment, the at least one processor is configured to execute operations at respective voice devices, the server, and/or additional distributed computer resources. According to one embodiment, the at least one processor is configured to generate an execution queue for the plurality of routines having overlapping execution times or triggers. According to one embodiment, the at least one processor is configured to generate the ordering of the execution based on a first in first out queue. According to one embodiment, the at least one processor is configured to generate the ordering of the execution based on priority assignment or determination associated with the plurality of routines. According to one embodiment, the at least one processor is configured to generate the ordering of the execution to include a secondary and subsequent ordering within respective priority assignment or determination. According to one embodiment, the at least one processor is configured to generate the secondary and subsequent ordering based on a first in first out queue. According to one embodiment, the at least one processor is configured to communicate routines for a set time period or trigger to an in-memory database, and the in-memory database is configured to manage ordering operations on the routines and distribution of the routines to respective user devices.

According to one embodiment, the system further comprises routine application programming interfaces (APIs) configured to accept external generation of routines for execution at the plurality of user devices. According to one embodiment, the at least one processor is configured to assign an execution priority to the routines generated via external systems. According to one embodiment, the at least one processor is configured to automatically customize an execution time or trigger of at least one routine in a group of routines having an overlapping execution time or trigger. According to one embodiment, the system further comprises a routine generation interface, wherein the routine generation interface is configured to prevent selection of overlapping timing of execution. According to one embodiment, the at least one processor is further configured to identify a currently executing routine conflicts with an upcoming routine and resolve the conflict based on ordering execution, delaying the upcoming routine, or rescheduling the upcoming routine.

According to one aspect, a computer implemented method for managing voice routine execution in a user environment is provided. The method comprises registering, by at least one processor, a plurality of voice devices, the plurality of voice devices comprising at least a speaker for communicating voice commands and a microphone for receiving voice input, wherein the plurality of voice devices are configured to enable assistance actions for respective users of the voice devices based on execution of voice routines; managing, by the at least one processor, execution of a plurality of voice routines, the plurality of voice routines having associated execution times or triggers; storing, by the at least one processor, primary versions of each voice routine of the plurality of routines; storing, by the at least one processor, a user profile for the respective user of the voice device specifying one or more voice routines associated with a respective voice device, wherein the user profile defines the associated execution time or trigger of the one more voice routines in the user profile; identifying, by the at least one processor, overlapping execution of a plurality of routines for one or more users; generating, by the at least one processor, an ordering of execution for the plurality of routines for the respective user; and managing, by the at least one processor, execution of the plurality of routines at the respective user's voice device according to the generated ordering.

According to one embodiment, the method further comprises executing operations at respective voice devices, the server, or additional distributed computer resources. According to one embodiment, the method further comprises generating an execution queue for the plurality of routines having overlapping execution times or triggers. According to one embodiment, the method further comprises generating the ordering of the execution based on a first in first out queue. According to one embodiment, the method further comprises generating the ordering of the execution based on priority assignment or determination associated with the plurality of routines. According to one embodiment, the method further comprises generating the ordering of the execution to include a secondary and subsequent ordering within respective priority assignment or determination.

According to one embodiment, the method further comprises generating the secondary and subsequent ordering based on a first in first out queue.

Still other aspects, embodiments, and advantages of these exemplary aspects and embodiments, are discussed in detail below. Any embodiment disclosed herein may be combined with any other embodiment in any manner consistent with at least one of the objects, aims, and needs disclosed herein, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. The appearances of such terms herein are not necessarily all referring to the same embodiment. The accompanying drawings are included to provide illustration and a further understanding of the various aspects and embodiments, and which are incorporated in and constitute a part of this specification. The drawings, together with the remainder of the specification, serve to explain principles and operations of the described and claimed aspects and embodiments.

BRIEF DESCRIPTION OF THE DRAWINGS

Various aspects of at least one embodiment are discussed herein with reference to the accompanying Figs., which are not intended to be drawn to scale. The Figs. are included to provide illustration and a further understanding of the various aspects and embodiments, and are incorporated in and constitute a part of this specification, but are not intended as a definition of the limits of the invention. Where technical features in the Figs., detailed description or any claim are followed by reference signs, the reference signs have been included for the sole purpose of increasing the intelligibility of the Figs., detailed description, and/or claims. Accordingly, neither the reference signs nor their absence are intended to have any limiting effect on the scope of any claim elements. In the Figs., each identical or nearly identical component that is illustrated in various Figs. is represented by a like numeral. For purposes of clarity, not every component may be labeled in every Fig. In the Figs.:

FIG. 4 is a table describing application and content, capability and voice device features, according to one embodiment;

FIG. 7 is a visualization of a routine and scheduling allocation, according to one embodiment;

FIG. 11 is an example screen capture of user interface for managing care recipients, according to one embodiment;

FIG. 13 is an example screen capture of a day to day view of scheduled routines, according to one embodiment;

FIG. 15 is an example screen capture of a routine generation interface, according to one embodiment;

DETAILED DESCRIPTION

Figure 1:
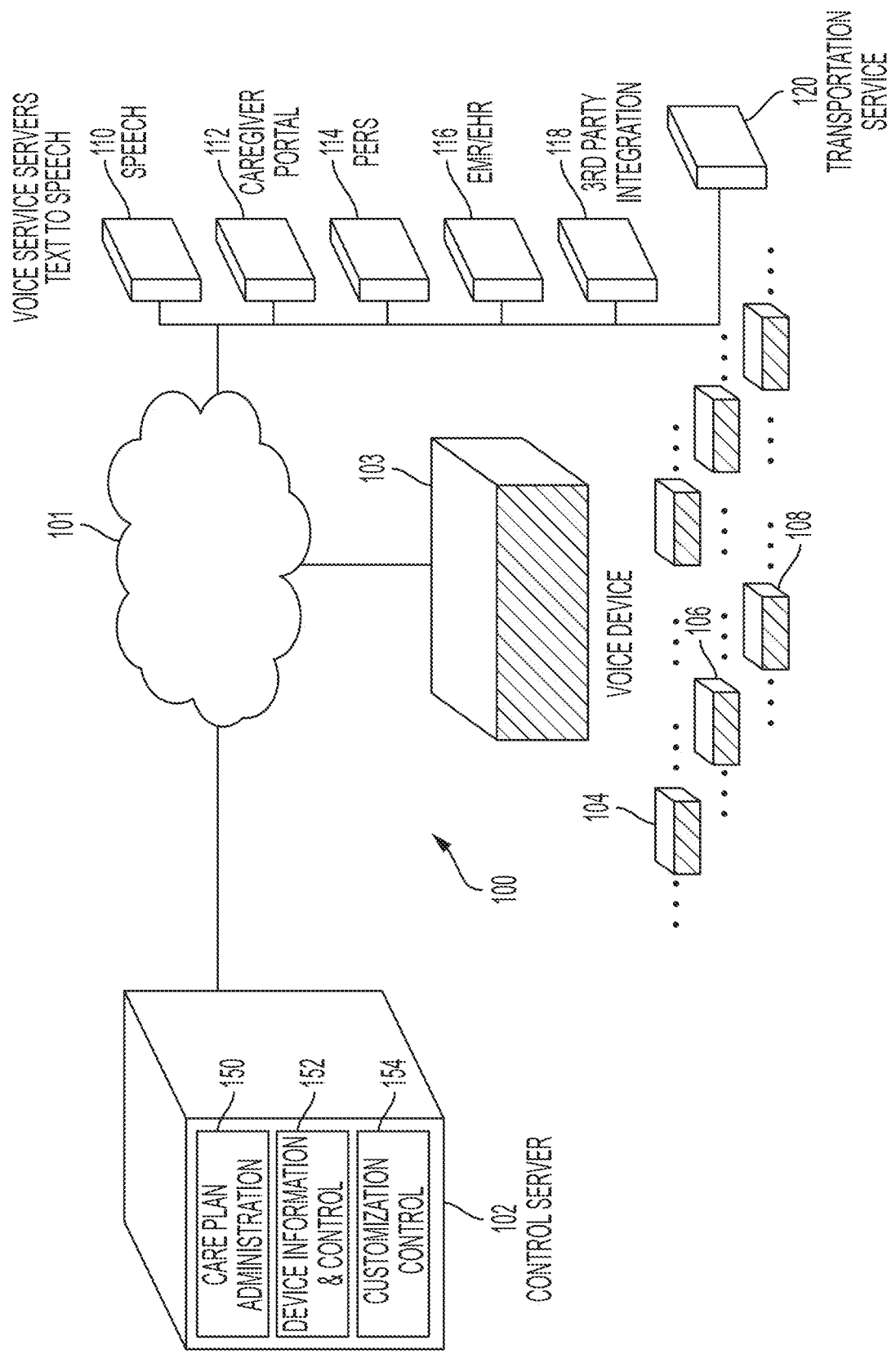
FIG. 1 is a block diagram of a voice assistance system, according to one embodiment.

Stated generally, a voice assistance system, which can include pre-configured routines, enables development, management, and execution of groups of voice services and voice enabled functions that provide both proactive and reactive functionality. In some embodiments, the groups of voice services define baseline operations for groupings of devices and/or device users. These groupings of voice services can include specific sets of instructions (e.g., routines, care plans, reminder services, notification services, etc. which can be delivered proactively or reactively), and can further implement basic services that are needed by large groups of users. For example, in a health care setting, a health provider or clinician can define a basic set of functions for a group of users and associate those voice routines with groups of user devices before sending the devices to respective users. In further example, devices can be pre-configured with proactive voice routines that can be defined by health providers, entities, or other institutions as part of distribution or registration of user voice interactive devices. In still other examples, grouped devices can also be managed as a group once they are installed. According to one embodiment, devices and/or users can be added or removed from such groups to provide additional options for managing voice service on respective devices.

In further aspects, making voice devices useful beyond reactive weather and time requests, presents unique challenges. For example, to improve utilization, such devices can be configured to be deployed at large scale with pre-configured voice routines (e.g., reactive and/or proactive routines). In some settings, an administrator or privileged user can customize selection of the voice routines that are preconfigured for various devices. Further, the administrator or the privileged user can customize selection of the voice routines for deployed devices. In one example, the administrator can select options within various user interfaces to pre-configure sets of devices with the selected functions. Returning to the health care example, a health administrator can customize sets of functions (e.g., medication notifications, medication timings, care instructions, doctor visit scheduling and transportation, etc.), for delivery of those pre-configured devices to groups of their customers. Thus, the health administrator can select and tailor pre-configured voice functions that can be based on selected group functions to include or can be based on various combinations of voice assistance routines. In one example, the system can present user groups or function groupings that are the most useful across a user base associated with the health administrator. The system can further provide the ability to customize and/or update voice functionality as target users' needs change, update, or evolve.

As discussed above, customization of functionality can be challenging when pre-configured functionality is defined on a device, for a user, or groups of users and the user population wishes to customize, create new, or alter pre-defined functionality. For example, where customization can include termination of specific functions, the system can be configured to balance a need or necessity associated with the given function against the user request. In addition, various embodiments of the system can be configured to prevent, minimize, and/or avoid conflicts that would result from user customization. The inventors have realized that customization opens the door to various conflicts, that include, for example, overlap in time, conflicting instruction, overwhelming users (e.g., care recipients, care providers, etc.), reduced compliance, external task generation and integration, etc. In other examples, overlap can result from a prior routine execution period running into a next scheduled task.

In various embodiments, the system is configured to architect various routines, groups of routines, and their customization to permit the greatest flexibility to the user base while minimizing the potential for conflict and/or resolving any resulting conflict. In some embodiments, routine queues are implemented when multiple sets of routines are set to execute. Further embodiments can implement priority statuses for respective functions (e.g., routines, sequences of routines, assistance actions, etc.), which can be used to adjust queue execution or the sequence of execution. In other example, delays can be triggered on queued routines, and priority information can be used to select routines for a delay as well as length or timing of such delay. In further example, a currently executing routine can conflict with a later schedule routine, and the system can resolve the resulting conflict as discussed in greater detail below.

Examples of the methods, devices, and systems discussed herein are not limited in application to the details of construction and the arrangement of components set forth in the following description or illustrated in the accompanying drawings. The methods and systems are capable of implementation in other embodiments and of being practiced or of being carried out in various ways. Examples of specific implementations are provided herein for illustrative purposes only and are not intended to be limiting. In particular, acts, components, elements and features discussed in connection with any one or more examples are not intended to be excluded from a similar role in any other examples.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

FIG. 1 is a block diagram of an example system 100 for managing voice routines. Shown in FIG. 1 is a control server 102 that interacts with a voice device 103 to provide any number of functions and/or services. The control server 102 can be associated with any number of voice devices (e.g., 104, 106, 108, etc., where the " . . . " illustrate any number of additional voice devices). In various embodiments, multiple control servers 102 can be present to manage large device population (e.g., thousands and tens of thousands of voice devices). Examples of the functionality managed between voice devices and one or more control servers (e.g., 102) is described in commonly owned U.S. patent application Ser. No. 16/936,019 (the '019 Application), filed on Jul. 22, 2020, which includes examples of operations for managing assistance actions, emergency services, caregiver operations, care recipient operations, proactively generating voice requests, proactively triggering voice services, among other options. The '019 Application is incorporated herein by reference in its entirety.

In various embodiments, the control server 102 and any associated voice device (e.g., 103) can be configured to deliver reactive (e.g., user triggered requests for functionality) or proactive (e.g., services initiated remote from the user or device) services in response to verbal requests. Further embodiments provide for integration of various sub-systems and/or third party hosted services over communication network 101. For example, the system can manage interactions with voice service servers (e.g., text to speech subsystems, speech to text subsystems, natural language processing subsystems (e.g., 110), caregiver portals (e.g., 112), personalized emergency response services ("PERS") (e.g., 114), emergency medical services ("EMS")/ electronic medical records ("EMR") (e.g., 116), and other third-party systems for integration and use of voice service (e.g., 118), among other options). In some examples, third-party systems can include transportations services and/or systems, notification services and/or systems, music delivery services and/or systems, news delivery services and/or systems, weather delivery services and/or systems, among other options.

In various embodiments, system integration can include integration of transportation services and systems provided by specific partners (e.g., 120). For example, a routine executed by the system when scheduling a doctor visit can trigger schedule of transportation via service 120. In another embodiment and/or alternative, scheduling at the doctor's office can trigger a transportation request on system 120, which is used to create new routines (e.g., reminder of ride request and preparation instructions) that can be proactively delivered to a user's device (e.g., 103). In on example, an application programming interface ("API") can be configured to handle routine creation based on actions taken on external and/or integrated systems (e.g., 110-120). In various embodiments, the control server and/or voice device can include multiple APIs for interaction with associated services and/or functionality. In some examples, the respective API can be pre-configured as part of group settings, and automatically prepared by the system to enable certain functions defined for a group.

According to some embodiments, the control server 102 can include a care plan administration component 150 configured to define various sets of functions, routines, features, etc., that are enabled on voice devices (e.g., 103-108) managed by the system. Stated broadly, the administration component 150 is configured to enable deployment of hundreds and thousands of voice devices as a collective. For example, devices associated with a corporate entity can number in the tens of thousands, and each device can be pre-configured with tailored functionality to support a user in their operating environment. In further example, the system can support access by health provider entities and pre-configure tens of thousands of devices for the health provider's user base. In still other examples, existing devices can be brought into group management by registering the device with the system, and a simple addition of the respective device to a group. In response to the addition, the system is configured to install or update any functionality of the respective voice device and schedule such functions for use by the end user of the device, with little or no interaction required.

In various embodiments, the administration component 150 provides access to authorized users to user interfaces that enable selection of routines and functionality that will be enabled on voice devices (e.g., at distribution and/or as updates to the respective devices, among other options). In the health provider example, a health administrator can be given access to define entity wide functions to configure on the devices. Selection made in the user interfaces, including routine customization, can be used to define functionality profiles for the entity, and any changes in entity profiles and included devices can be propagated throughout deployed devices, as well as updating configurations for devices that will be deployed. The system can also provide additional organization within an entity to target smaller groups, or groups having characteristics in common.

In one example, a caregiver can be associated with a group of users and their devices. The caregiver can access the system and/or user interfaces to customize the entity profile and functions, where the customization is associated with the group of users and devices. In one example, the caregiver can be a health professional tasked with day-to-day care for a group of users. In addition to customizing the entity profile and/or functions, the caregiver can create or add new routines for the group. In various examples, the system can provide a plurality of access levels to care plans and administration functions to provide group definitions at entity levels, departments within entities, groups of users associated with an entity, etc. Unlike conventional deployments of known voice service devices, the system enables configuration and updating of functionality across massive user populations and their devices with simple selections in display user interfaces.

According to various embodiments, user groupings can be maintained on a control server (e.g., 102) or other remote system configured to manage deployment of voice services and/or associated devices in various settings. According to one embodiment, a grouping and/or groupings of voice services can be tailored to a specific corporate entity, employer, or other service provider, institution, association, among other options. In some examples, proactive and reactive voice routines can be grouped together or grouped separately, among other options. For a large deployment of devices, the voice assistance system can enable such groups of services and/or selections of multiple groups of services by default that are tailored to respective use environments and/or user populations.

In further embodiment, the system can include a device information and control component (e.g., 152) configured to register or associate voice devices to specific users, entities, and/or groups. In further embodiments, each device can include multiple user profiles and each user profile can be assigned or associated with different groups, entities, and/or custom routines. In various embodiments, the device component 152 can be configured to manage authentication and identification of appropriate user profiles and associated functions. Identification and authentication can be based on analyzing verbal input (e.g., voice print, etc.), as well as requesting identification information in the form of username, passwords, etc. Identification and/or authentication can be executed on the control server 102 and/or at a respective voice device (e.g., 103).

In some embodiments, the control server can include a customization control component 154. The customization control component 154 can be configured to manage operations to customize user routines. In one example, the component 154 can be configured to monitor requests for new routines, alternations to existing routines, deletion of routines, and control any create, read, update, and delete ("CRUD") operations on routines. As discussed, various routines can be associated with priority information which limits the ability to create, read, update, and delete specific routines or to create or update routines that may conflict. In various embodiments, the component 154 can be configured to manage requests to customize routines and evaluate priority information associated with a routine being customized as well as any routine that would be affected by the customization. In one example, the system evaluates time periods associate with sets of routines to determine if a new or altered routine can be executed by queuing multiple routines. If the result is positive the request is confirmed. If the queue may be insufficient, the request can be adjusted in time to allow for execution, and the update communicated to the user. In other examples, the system can identify options for resolving, and communicate a request for a preference from the user on which routine to delay.

According to one embodiment, the system can be configured to avoid conflicts in generation and/or customization (e.g., via component 154). Various settings and/or architectures enable the system to evaluate customization requests and resolve specific conflicts, including those based on need or necessity as well as those based on timing and/or processing capacity. In a health care setting, the system can recognize a request to terminate routines for medically necessary functions (e.g., medication) and reject or reformat such customizations. In the alternative and/or in another embodiment, the system can determine if a baseline or default function has been replaced by a customized function, and the system can permit de-activation of pre-configured "necessary" routines in favor of a customized user routine. In other embodiments, the system is architected to minimize conflict space in generation and/or management of default or group-based routines or functions. Not only are various embodiments configured to ensure medically necessary functions are executed, but the system can also be configured to avoid conflicts that result from user customization. In some examples, time division functions are used to avoid conflict, and in others locking mechanisms that make some routines immutable absent release of a lock can be used to avoid conflicts. For example, routines can be created and/or defined on the system that specify action to be taken on a user device, where each action (e.g., voice input request, confirmation request, assistance action, analysis, communication, etc.) can be associated with a duration for execution. In additional to maintaining durations associated with individual actions, groups or sequences of actions, the system is configured to manage time assignments to respective actions. Time slices can be selected and/or re-serviced to minimize or avoid conflict with customization of respective actions by the user. In one embodiment, the system is configured to implement time slices associated with a specific duration (e.g., the specific duration can be tailored to selected actions, or be assigned by the system based on group of actions to be configured (e.g., shortest action duration can be assigned to duration of the time slice, average duration, longest durations, multiple of shortest and/or longest, among other options). Other options to manage multiple routines and execution are discussed in greater detail below.

Figure 2:
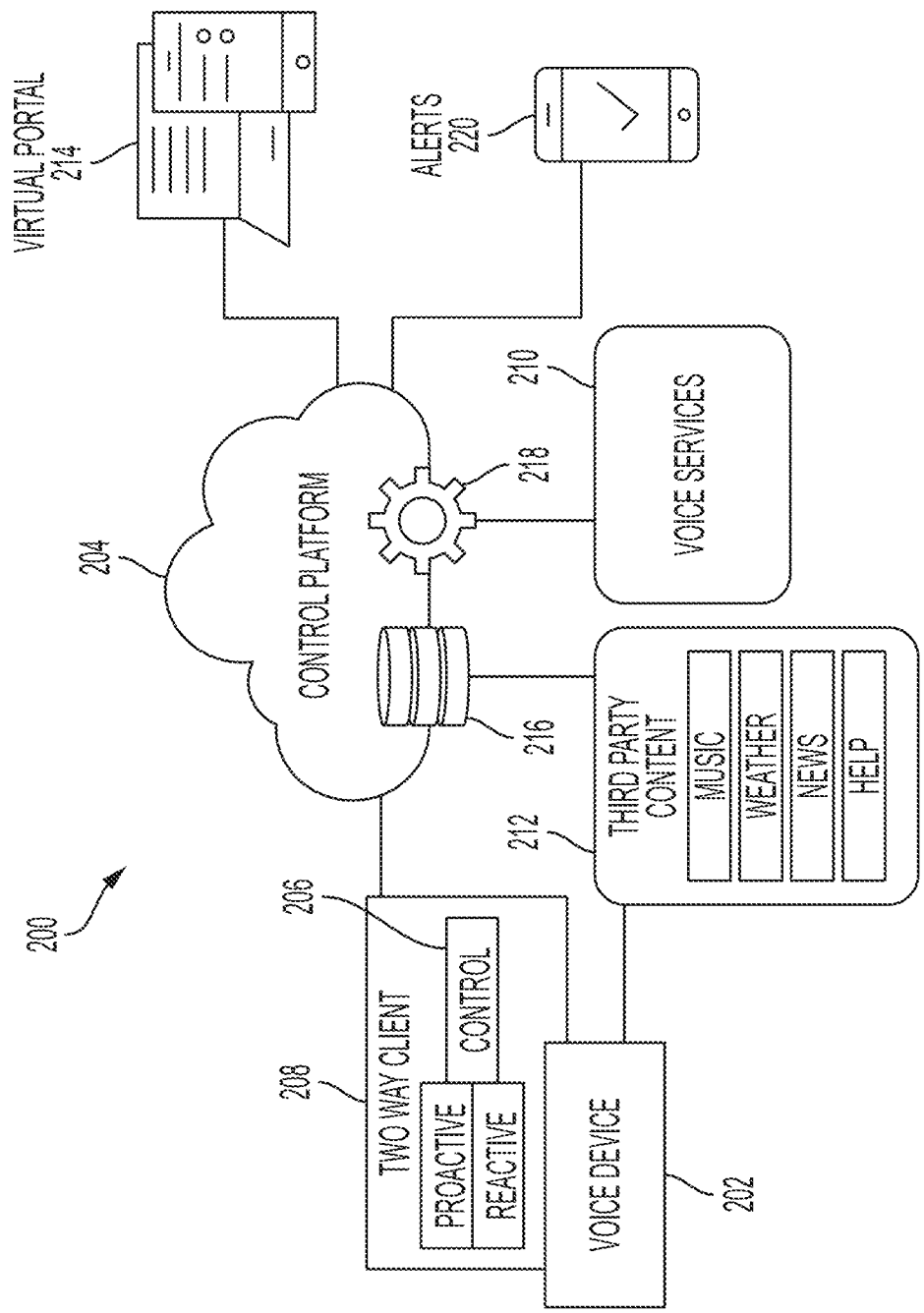
FIG. 2 is a block diagram of a voice system and control platform for managing assistance actions, according to one embodiment.

FIG. 2 illustrates an example environment 200 in which a voice device 202 can interact with a control platform 204 to deliver proactive and reactive voice services 206 via a two-way client 208 on the device. Any number of voice services can be configured to execute on the voice device 202. The voice services available on the device can be pre-configured based on group membership defined on the control platform 204 and/or can be managed based on group membership defined on the control platform 204. According to some embodiments, the voice service can include speech to text and natural language processing, as well as text to speech to facilitate execution of voice routines (including, for example, assistance actions for a device user who is a care recipient, as well as other services).

In further embodiments, administrators can access the control platform 204 via a virtual portal 214. The platform can provide access to multiple user types, multiple entities, etc., via different or tailored portals and displays. In some examples, entities can access an entity tailored portal with an associated entity administration user and privilege. In various examples, the entity privileged user can define routines and groups of routines on the system for the respective entity (e.g., health organization, health care service provider, corporation, etc.). In further example, the entity privileged user can associate members/device users and their associated devices to the organized groups of routines. In response to the assignment, each device is configured with the routines and/or supporting functionality for the routines. Unlike conventional voice devices where the burden to install or update configurations is on the user, the control platform can be used to manage distribution, configuration, and updating of thousands of voice devices. Within entities, lower-level permissions can be assigned, which include user group privileges. For example, in the health and assistance environments caregivers can be assigned group administrator privileges. In one example, a caregiver can be responsible for a number of care recipients in a health care organization. The caregiver can access a caregiver portal (e.g., 214) to assign care recipients to routine groups (e.g., group level organization). In further embodiments, the control platform 204 can enable caregivers to have access to entity level groups and group level groups. Shown at 220, voice routines can include specification of alerts to be sent when routine conditions are triggered. The '019 Application describes example conditions, alerts, and user profile definitions that can be customized as discussed herein to generate alerts (e.g., 220).

In further embodiments, group administration can be limited in access to routine groups and ability to assign users/devices to routine groups associated with a group administration role. In other embodiments, different entities (e.g., corporations) can have entity level administrators and entity level routine groups, as well as group administrator users (e.g., manager with subordinates as device users, etc.). Other access levels can also be configured on the control platform (e.g., ability to add devices to a specific group, or select group, ability to customize routines within in a group, etc.).

According to another embodiment, voice routine groups can be customized by or based on system intelligence. For example, the control platform 204 can be configured to capture user information, device information, and behavior information captured as part of routine execution, among other options. For example, the control platform can include a datastore 216 for storing demographic information, as well as behavior and/or interaction information from respective devices. The stored information can be processed by artificial intelligence ("AI") 218 to identify commonality between entity users and identify likely candidates for inclusion into routine groups. In some examples, the platform can surface these identifications to administrative users. In some embodiments, the administrative user can be shown display groupings of users with commonalities identified by the machine learning algorithms, so that the administrator need only select the users with commonality in the display and add them to respective groups. In further example, AI can filter or display likely group matches in prominent positions in the user interface to facilitate selection. The AI models can also be configured to identify routine groups that match characteristics of users or user groups. For example, the system can use AI matches to filter or display routines groups in the user interface. In one embodiment, the user interface can include a display portion that identifies AI based matches (e.g., routine groups, users to add to user groups, etc.) to facilitate management of routines, users, and/or devices.

According to some embodiments, information captured and stored in data store 216 can include information on customization made by user populations. AI models can be used to train on characteristics of customizations selected by users, characteristics of users making customizations, and/or characteristics of both. In one embodiment, the AI models are used to identify customization(s) to routines that are likely to benefit an entity, routine group, and/or individual user. In one example, the AI model can surface the customization information as a selection in the user interface. Acceptance in the user interface by an administrator can implement the change identified by the AI model. In other examples, customizations identified by the AI can be made on the platform and monitored to determine effectiveness/acceptance of the AI identified change. Feedback from the user population can be used to conform the AI model and/or refine the AI model. In some embodiments, platform-based customizations can be made with automatic rollback functionality. For example, a user can be informed of a change to a routine and given the option to reverse the customization. In some examples, the control platform can be configured to distribute a customization package that includes instructions for reversing any change. In one example, a customization from the system side can include verbal requests announcing the customization and identifying a trigger word to restore prior settings. In some examples, the system can notify the user that the system will check-in again in a certain time period to confirm the change and/or provide a roll-back option. In some embodiments, the system is configured to automatically create new check-in routines in response to updates, and provide an option to the user to roll-back an update to a prior state using a spoken command identified as part of the check-in routine. Various entities access the platform and establish their preferences for controlling their entity level routines, group level routines, individual routines, and the management of the same.

Figure 3:
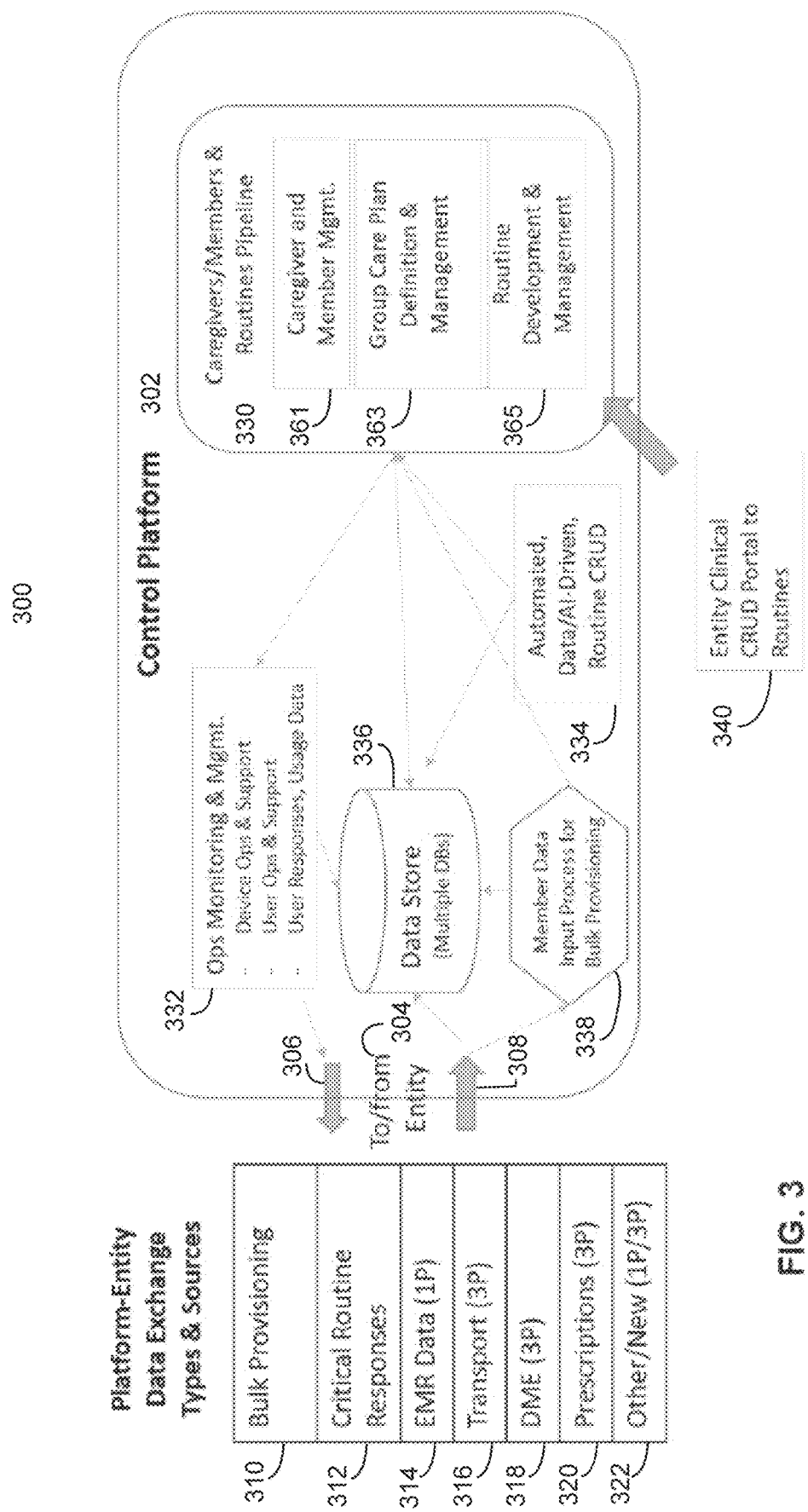
FIG. 3 is a block diagram of a voice system and control platform for managing assistance actions according to one embodiment.

FIG. 3 is a block diagram of an example system 300 including a control platform 302 and support systems associated with a connected entity 304. In this example, system 300 illustrates an example healthcare entity (304). In some embodiments, the entity and platform are configured to exchange data which can be managed based on type and source of data. For example, information flows are shown at 306 and 308. The exchange of information can include information on bulk provisioning of devices (e.g., 310), critical routine responses (e.g., 312), EMR data (e.g., 314), transport (e.g., 316), durable medical equipment—"DME" (e.g., 318), prescriptions (e.g., 320), and other information or new information (e.g., 322) on users, devices, routines, among other options. The examples shown at 310 through 322 are intended to illustrate the types of data and sources and are not limiting.

As discussed above, the control platform 302 is configured to manage a multitude of user devices, and can also be configured to manage bulk provisioning of voice service devices to entity members/users. For example, the control platform 302 can include a data store 336 which may be made up of multiple databases each tailored and designed for respective functions on the control platform. In one example, a member data database (e.g., 338) can store information for linking entity members/users and devices to be managed and/or distributed.

According to some embodiments, member data can be used for linking users and/or devices to routines and functions available on their respective devices. For example, the control platform 302 can include the routine management component 330. The routine management component can be configured to control routine development and management, group care plan definition and management, caregiver definition and member management, among other options. In some examples, the routine management component 330 can include subsystems or subcomponents that are dedicated to the functions and operations described above. In one example a caregiver and member management component 361 can be configured to control registration of members, member demographic information, association with devices, among other options. In another example, a routine management component 330 can include a routine development and management component 365 configured to allow users (e.g., administrators) to create routines that define actions to be taken with respect to voice devices and assistance actions (e.g., reactive and/or proactive). In further example, collections of routines can be created to define care plans, wherein the collection of routines can define a treatment care plan, a long-term care plan, and short-term treatment plan, and/or a chronic treatment plan, among other options. In other examples, the care plan can define a course of treatment or activities that a user should take with respect to a medical diagnosis, a medical condition, among other options.

According to some embodiments, care plans can include assignment of caregivers to respective members. As described above, a management component 361 can be configured to link caregivers and members, and may do so according to the diagnosis, condition, treatment, specialty, etc.

Depending on the user/member and any associated conditions or functions desired, an operation management component 332 can be configured to manage configuration of user devices to support that condition or desired function. In various embodiments, the operation component 332 can be configured to manage devices, manage operations enabled on the devices, manage user associated operation, manage user support for devices and/or functionality enabled on a device. In still other embodiments, the operation management component 332 can also be configured to handle user responses received from respective devices. User responses may include verbal queries, verbal answers, verbal inputs, text inputs, etc. The operation management component 332 can also be configured to monitor usage data associated with user devices and/or user behavior associated with respective functionality and/or operations.

In various embodiments such information can be managed in a data store (e.g., 336), which may include databases specific to each set of data. Various administrative users can access the control platform and management functions to set associations for users and devices, to add new users, to create new voice routines, to create new care plans (e.g., groups of routines), and or to manage members and associated caregivers. In one example, an entity can access an entity portal to manage routine selection for their members (e.g., 340) and/or manage assignment of routines into packages or sets of routines used by groups or cohorts of users. The packages can be defined by an entity (e.g., a healthcare organization) or by the control platform administration. In various examples, the functionality is defined to facilitate deploying thousands of voice devices with tailored functions pre-configured. In one example, entity members/device users are setup with default routine packages or care plans matched to their demographics and/or information. The default packages can include default timing for each and any routine defined in the package (e.g., default schedules to start routines), but with enhanced capability to accept, develop, and deploy personalized routines, at scale.

According to various embodiments, the control platform is configured to ensure baseline functionality for each user and/or device. The baseline set of functions can be tailored to respective entities and their user population. For a healthcare organization an example set of baseline functionality for a voice device can include any one or more and any combination of the following: configuration to speak and understand multiple languages, configuration to administer surveys and communication results to a requesting entity, configuration to generate personalized reminders based on third party information (e.g., external system integration, etc.), configuration to schedule transportation rides (e.g., via platform configuration and/or third party service integration), capture and report on durable medical equipment "DME" status (including, for example Medline and/or McKesson equipment, etc.), generate and provide medication reminders (including for example platform routine reminders and external generated routine reminders (e.g., via eClinicalWorks "eCW" or other third-party system)), proactive routines to manage medication refills (which can be executed through MedMinder, PBM, etc.), configuration to send specialized routines to members based on diagnosis associated with the user, configuration to send specialized reminders to members based on care plan assigned to the user, configuration to enable personalized additional content (news, weather, music), configuration to connect with other monitoring devices (e.g., IoT devices, PERS, weight scale, blood pressure monitor, Fitbit, Apple watch, etc.), among other baseline configurations.

Some baseline function sets can include functionality in addition to and/or in alternative to the above list, which may include any one or more and/or and combination of the following and any combination with the above functions: conduct surveys for dental providers, pharmacy providers, and member feedback, voices; reminder routine creation and maintenance for any one or more or any combination of the following: transportation services; appointments (e.g., health care providers, doctors, clinicians, etc.); medication (e.g., dosing, timing, customized to user (e.g., weight, comorbidities, other medications, etc.)); prescription refills (medication, DME (e.g., medicinal deliver systems, etc.), etc.); management, customization and/or creation of routines; status routine creation and maintenance for key action items from members' care plans (e.g., care based entities and/or caregivers can designate priority levels for care actions as part of care routine definition, likewise control platform administration can designate priority levels for any action (e.g., care actions) to be executed with a voice device as part of routine definition); key action items can include for example, DME inventory, as well as supplies receipt/ inventory, authorization status (e.g., for caregivers, and other persons (which can be set at various levels, including decision based (e.g., approval only) rather than routine creation/modification)), among other options.

Further baseline function sets can include functionality in addition to and/or in alternative to the above list, which may include any one or more and/or any combination of the following and any combination with the above functions: enroll members (e.g., register users and/or devices) in routines based on, one or more or any combination of the following criteria: disease diagnosis (e.g., diabetes, COPD, nutrition deficiency, etc.), desired behavioral changes (e.g., smoking cessation, diet, exercise, ADL support, etc.), temporary needs (e.g., wound cleaning, post-discharge plans, etc.), among other options. Various embodiments can further tailor baseline function sets to include routine management, customization, and/or creation to support personal care attendants & at home assistance. In some embodiments, each of the functionalities discussed above can be made available to administrative users as selections in various user interfaces. For example, the administrative user can enable baseline functions, or groups of baseline functions, which results in their display for associating users/devices with respective routine groups that are based on those functions.

FIG. 4 is a table showing functionality that can be managed by the system. As shown, various functions can be described based on their application and/or content (e.g., column I) provided to an end user of a voice device. Further, the system can manage the various functions according to how the capability is rendered by the devices. For example, "C.R.U.D." references create, read, update, and delete functions used by the system to allow the application (content) to be provided. Last, the system can also use a feature context to manage access and control routine management associated with the functions. For example, "personal" is the context in which a user typically selects and/or accesses functions for detailed news/music/weather options. In further example, the user is enabled to utilize routines that will present any one or more detailed news/music/weather options as proactive routines or reactive routines tailored to their preferences. In some examples, this functionality is bundled into a device distribution that pre-tailors a voice device for the user before they ever speak to it. In further example, the system can manage (and/or pre-configured) the various applications described in column I. The system can also be configured to manage those functions in conjunction with external system, entity managers (e.g., who assign routine groups to users/devices), and device users (e.g., can create their own routines), among other examples. In some embodiments, the column II of FIG. 4 describes a source or multiple sources for a capability. For example, "AI-Generated" describes the system functions that used AI models to select, create, and/or modify routines or sets of routines for users. In another example, care plan connection describes associating a device/user to a routine or set of routines to enable the application (content) of column I. Other capabilities include: "care plan connection (temporary)" to connote a routine/set of routines with a definitive lifespan using routine administration functions, "member initiated" to connote a routine/set of routines generated by a user, care plan connection to connote a recurring routine selected using routine administration functions, "vendor connection" refers to routine creation from external (e.g., third-party) systems (including, for example, API integration into a transportation service that can create proactive reminders to a user to anticipate and/or prepare for a ride request scheduled on a third-party system), "device development" refers to functions (e.g., inventory/supply management, replenish and/or install disposable units, etc.) developed to support assistance devices in a user location (e.g., PERS devices, medicinal administration devices, monitors, etc.), "language utility" to support various languages, "surveying" refers to user interaction and feedback which can be on behalf of the platform, entities, and/or third-parties, "critical routine" refers to a routine having an elevated importance or priority assignment that should be used by the system to establish execution precedence (e.g., third-party scheduled functions, medically necessary functions, caregiver/health care provider assigned priority, etc.). In some examples, the system can resolve execution precedence based on capability category (e.g., critical routine versus member-initiated reminder or surveying). In other embodiments, capability categories are used by the system to determine what system-based functions can be used to manage, modify, delete, and/or customize routines.

In further embodiments, the system can assign feature classifications to various functionality. For example, the feature classifications can include any one or more and/or any combination of the following: "personal" to designate a user created function/routine, "reminders" to designate a function/routine responsible for providing a reminder to the user to perform an action (including, for example, care based actions or to prepare for future routines, among other options), "clinical" to designate medical or treatment related activities/routines, "status" to designate system or routine status for respective system operations and/or to determine authorization, "admin fxn" to designate operations to perform by the system or automated systems (e.g., replenish consumable supplies for medical devices), "language" to designate communication and language information/settings, "surveys" to designate information capture sessions via questions to respective users, among other options.

In various embodiments, the system includes many routines and/or sets of routines that administrative users can group and/or assign according to the membership the administrative users supervise. According to one embodiment, the routines are developed to provide various language interfaces and/or interactions. Translation operations can be executed on the system to transform a routine generated in one language into routines that interact with users in a multitude of languages (e.g., delivering verbal input request, reminders, etc. in not only the origination language but in any recipient language specified by a user profile, among other options).

Importantly, the system and/or voice device can be configured to support multi-language responses from users. In one example, the voice devices and/or the system (include, for example, a control platform) can be configured to recognize an input language based on a verbal response from a user and interpret the response regardless of the language used to respond. In still other embodiments, routine and/or set of routines can define multi-turn dialogs. In multi-turn dialog complex interactions between a user and a routine can be executed. For example, a first voice prompt can request permission to begin a complex routine, and upon confirmation, trigger a set of needed actions/request. To continue to the example, the user must have access to a medication administration device, must not have eaten within a period of time, and once the medication is administered, be connected or within a certain distance of a monitoring device.

Other examples include collection of routines that manage multi-turn care activity or other activities. Additional examples include treatment and care of COPD, CHF, ADLs, and can also include multi-step surveys and/or data collection, among other options.

The system can manage the multi-turn dialog to complete the routine or set of routines, handle any negative responses during the interaction (e.g., requiring reschedule or video connection, etc.), and multiple conversion pathways that deliver a complete routine, incomplete routine, and/or reschedule the routine, among other options.

In some embodiments, the system can include management of routines that are generated by third-party systems. For example, doctor office of members can connect to the system and/or control platform via APIs. The APIs can permit generation of reminders in response to scheduling doctor visits. For some users, the scheduling of a visit can also include scheduling of transportation services for a doctor visit, and the transportation system can be linked via an API which permit creation of reminder routines (e.g., "You doctor appointment is today—you have a car arriving at 1 p.m. to take you"). APIs are also available to integrate third party content, and can permit customization of third-party functions via voice inputs. For example, transportation, appointments, DME, medication refills, medication reminders, and/or streaming media can have associated routine that users can customize.

According to one embodiment, the system can include artificial intelligence to create routines, customize routines, and/or match routines to users. User data once associated with routine execution can be captured and analyzed to identify user populations that complete their activities at a better completion rate. In some examples, the higher completion rate users and their characteristics can be used to determine if the user, their caregiver, and/or customizations in their routines improve compliance. In some examples, machine learning models are trained to identify customization characteristic that improve routine compliance, and further models can be trained to match similar users. In some settings, the identification of customization and matching of users can be leveraged by the system to automatically suggest customizations for new users. Use of the machine learning suggestions can likewise be fed back into the machine learning model to improve the suggested customizations and/or user targeting for specific customizations, among other options.

In some implementations the system is tailored to provide a simple interface in which administrators can build and/or manage a variety of routines, preserve existing routines for a user while adding a routine or sets of routines without creating conflicts. In one example, the system provides a user interface that permits simple selections to simplify CRUD administration, for example, at a routine or a care plan package level, for both individual members and groups of members. In execution, the system enables simple design and development of CRUD operations on the system for any routine, group of routine, user and/or groups of users in the user interface ("UI"). In further examples, the system is configured to avoid any requirement of comprehensive conflict-checks at every add/change, minimize potential for contention between different types of routines (e.g., based on categorizing capability, functions, etc. coupled with execution ordering, time partitions for execution, delayed task execution, etc.), support quick resolution of contention/time conflicts that do occur via prompts in the UI, enable caregivers and algorithms to select a time slot for every routine as a default (e.g., enabling customization in the UI and by the user), minimize reliance on "random timing/scheduling" that could make play-times a mystery, etc.

The system can also be configured to manage routines so that one primary copy exists of each routine in a care plan/package/group of routines. The system can be configured so that if that routine is updated, the routine can be updated for all subscribers (e.g., associated users) to the plan requiring only a single record insert/update/delete to disseminate the changed across large user populations. In some environments, "primary" changes can be permissive—distributed but requiring user permission to enact the change. Some customizations to routines and/or packages can be assigned based on user classification—e.g., an early-to-rise version can include an offset time for starting routine execution, wherein an early-to-bed can include an offset for an end time and/or start time, among other options.

In further embodiments, the system can determine wherein a user is new to voice interactive routines and/or assistance interactions. In such settings, the system can provide an introduction version of a set of routines to limit the number of daily activities/interactions requested by a voice device. As the user becomes accustomed to voice interaction, the system can increase the number of routines being performed over time or move to the complete set of routines. In some embodiments, the system can identify routines to exclude or defer based on capability categorization or feature categorization, among other options.

Figure 5:
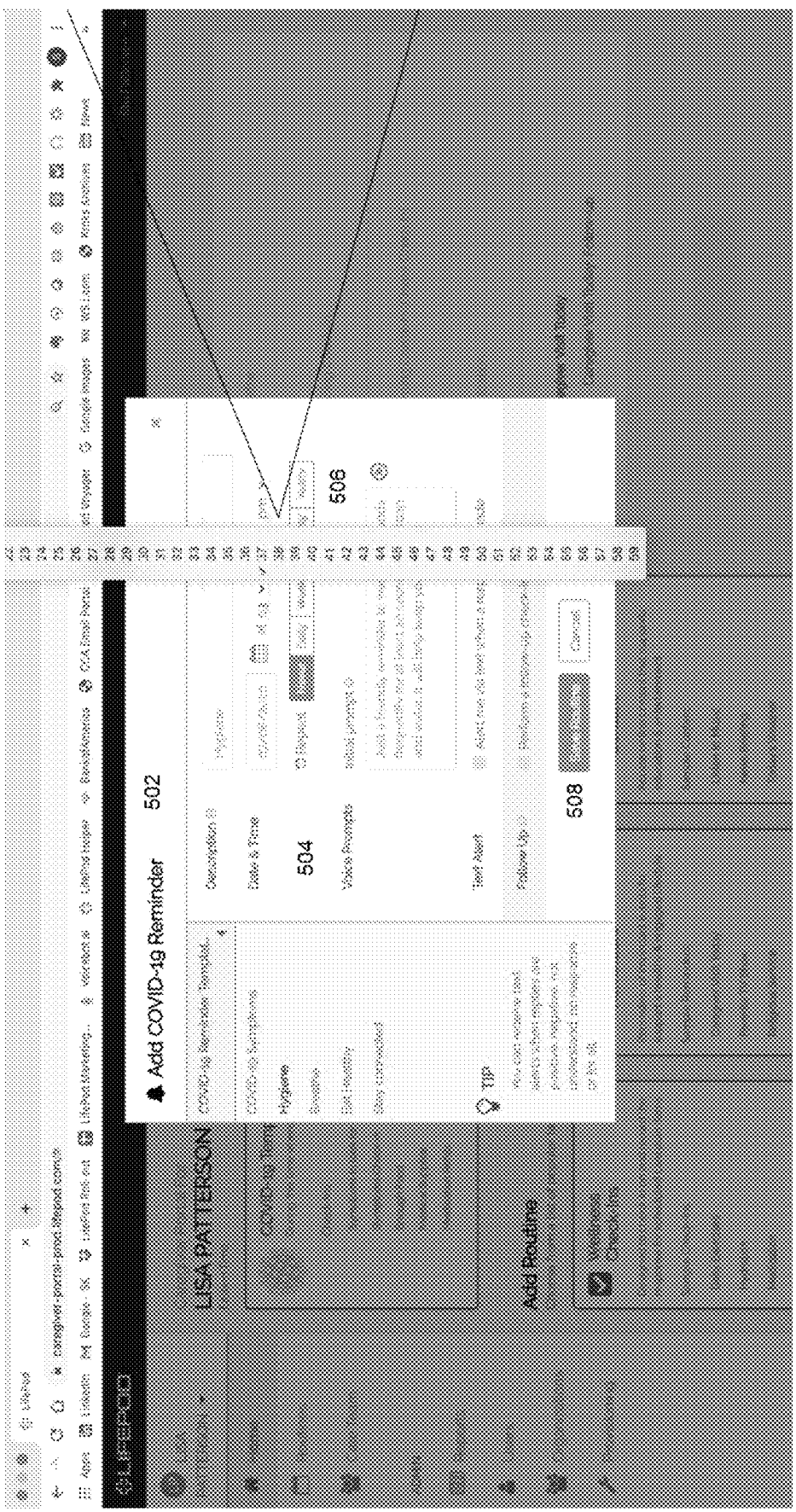
FIG. 5 is a screen capture of a user interface for routine creation, according to one embodiment.

FIG. 5 is an example screen capture of routine creation interface. As shown, the interface is selected to create a reminder routine for COVID-19 hygiene recommendations. The interface can allow the user to set a date and time (e.g., 504) for the reminder as well as a recurrence schedule (e.g., 506) (e.g., never, daily, weekly, monthly, yearly, among other options). As part of setting a date and time, the system can present hour and minute selections that can include scrolling displays for the same. In some examples, the system maintains information on routines scheduled for a particular user and graze out timing that would interfere with existing routines. According to some embodiments, multiple routines can be scheduled for the same time and the system will permit scheduling of any number, a fixed number, a threshold number, among other options numbers of routines for given time period. In other embodiments, the system maintains time division between routines to avoid conflicts. In some alternatives and or other embodiments, the system uses execution priority to resolve multiple routines having the same execution time.

According to one embodiment, the system can permit the user to enter any information into the routine creation interface and responsive to selection of save routine (e.g., 508) the system performs a conflict check for other routines scheduled at the same time.

Figure 6:
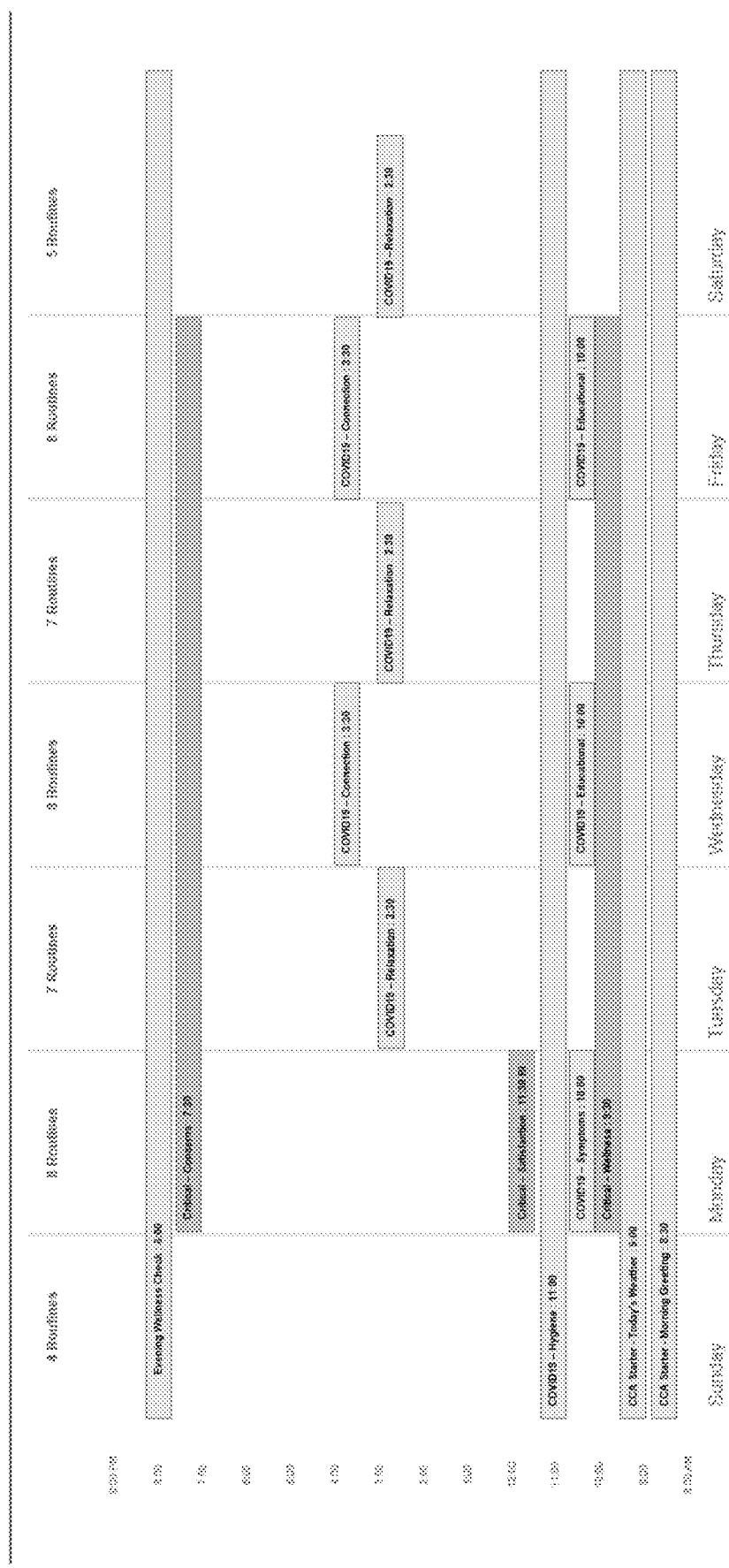
FIG. 6 is a Gantt chart showing example routine and scheduling, according to one embodiment.

FIG. 6 shows an example display scheduled routines for a user or user group. In the view shown in FIG. 6, an administrator can review how many routines are scheduled within a particular routine package or set of routines.

FIG. 7 shows an example screen capture of a routine schedule generated in response to adding a member to a set of routine packages. Shown in FIG. 7 is a time slot approach used to reserve timeslots for additional routines or routine packages.

Figure 8:
FIG. 8 is an example screen capture of user interface for managing routine and allocation, according to one embodiment.

FIG. 8 is an example screen capture of a user management screen shown as part of a caregiver portal for an associated member. In the display, the list of routines linked to the member (e.g., Carol Swift) are shown at 802. According to some embodiments, the list of routines is filtered to the routines that will be executed for given day. Navigation options shown on the left side of the screen (e.g., at 804) provide access to a suite of routines and/or all routines assigned to a given member. For example, at 806 selection in the user interface will trigger the system to navigate to a routine interface. Within the routine interface, a caregiver or other administrative user can create new routines, access routine groups, and/or assign existing routines to a user/member. Selection at 808 is configured to transition the system to a care team interface. The care team interface enables a privileged user (e.g., a care team member, or other admin) to assign caregivers to a user/member.

According to some embodiments, the interface is configured to display sets of routines (e.g., at 810) the system identifies as particularly relevant or important based on various factors (e.g., season, time, date, environmental, medically relevant, health and safety conditions, etc.). In some examples, the system can surface recommended routines based on artificial intelligence algorithms which are defined and/or trained to match specific routines to users, conditions, and other factors. In other examples, the system defined rules can establish what is displayed in the user interface in terms of routines of importance or a special significance.

According to one embodiment, the user interface can include displays of groups of proteins organized by type and/or category, among other options. For example, the system can display a list of "popular templates" in the user interface. In one example, the user interface includes displays for wellness checking routines at 812, social reminders routines at 814, and/or streaming content routines at 816. Additional routines, routine groups, and/or routine categories can also be shown in the display (e.g., home display 800).

Figure 9:
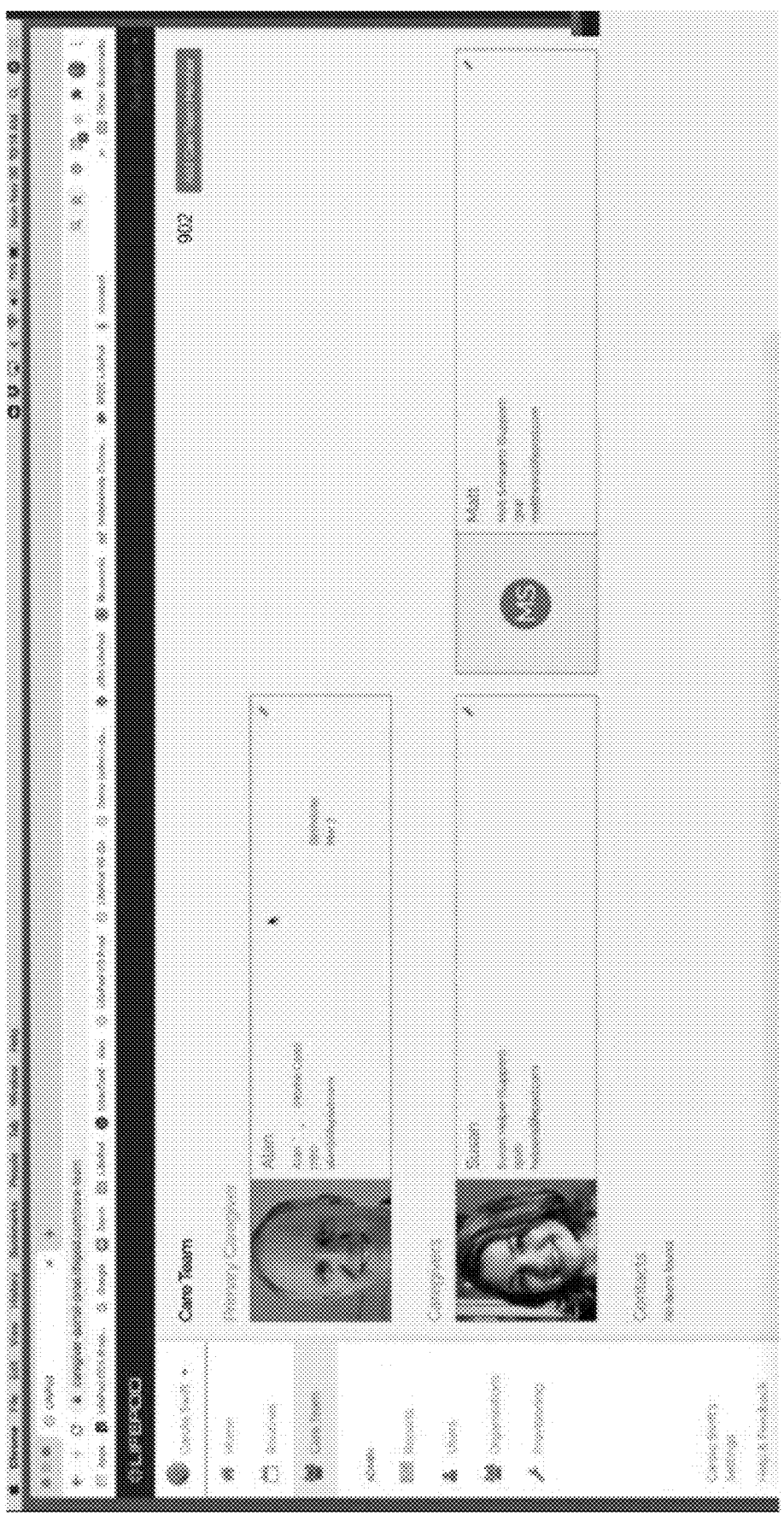
FIG. 9 is an example screen capture of the user interface showing the care team and associated functions, according to one embodiment.

Shown in FIG. 9 is an example screen capture of a user interface for managing a care team. Privileged users can add care team members by selecting the add button at 902. According to various embodiments, the system can be configured to assign a care team member and support staff to each member for specific entity by default. In other embodiments, a privileged user is given permission to create an initial care team assignment for any member/user.

Figure 10A:
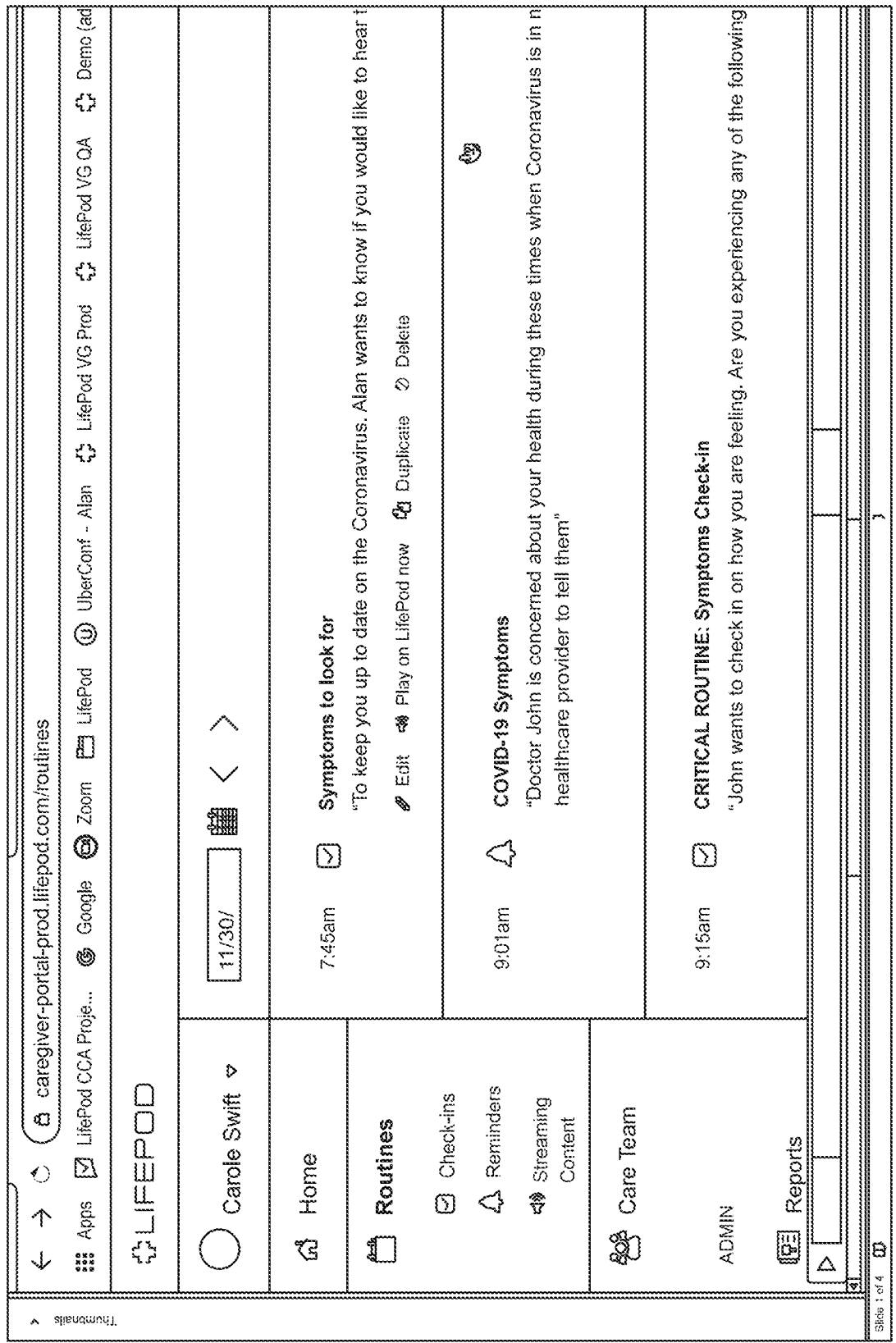
FIG. 10A-B is an example screen capture of a user interface for routine management, according to one embodiment.
Figure 10B:
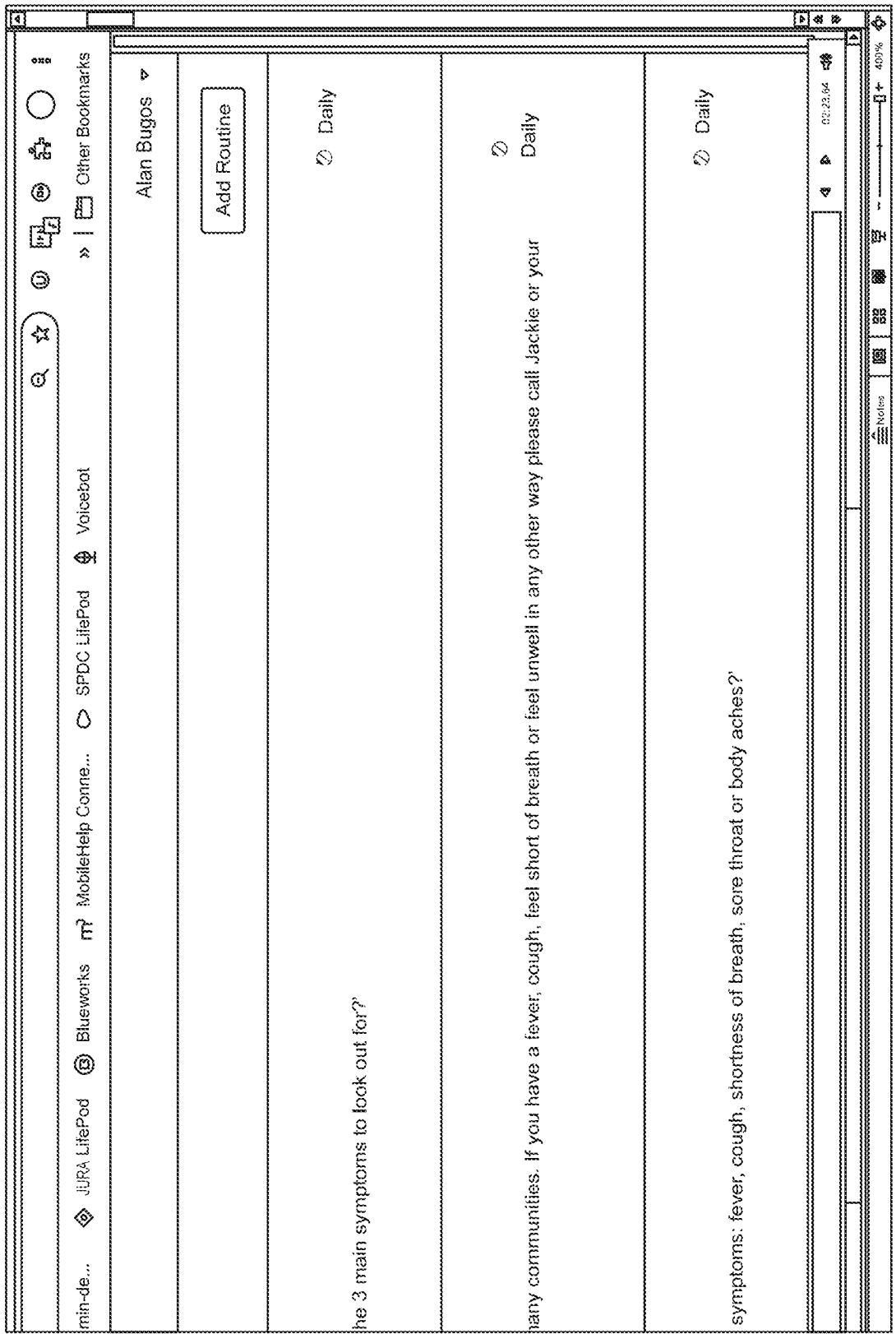

Shown in FIG. 10A-B is an example screen capture of the user interface for managing routines for a user. According to one embodiment, the user interface can include a default display format configured to show routines for a user by calendar day, and order the routines by time of day. In other embodiments, the user interface can include options to adjust the display settings (e.g., with a calendar icon in the upper left portion of the user interface) to reflect other time periods and/or ordering of routines.

Figure 11:
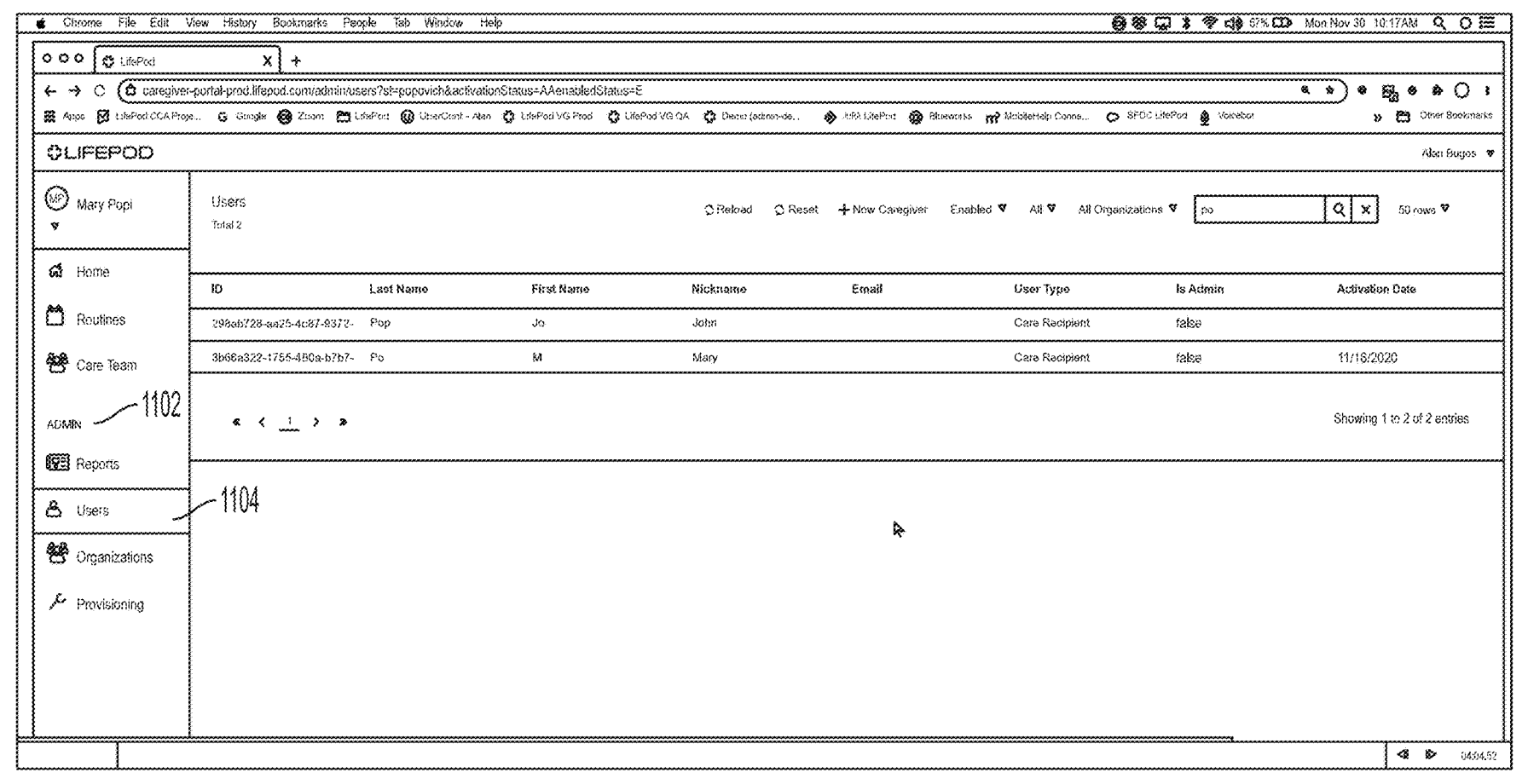

Shown in FIG. 11 is an example screen capture of a user interface for managing users on the system. The interface can be accessed by selecting administrative functions (e.g., at 1102), and for example, the user navigation display (e.g., 1104). The display can specify a user type (e.g., care recipient, caregiver, group admin, etc., at 1106).

Figure 12:
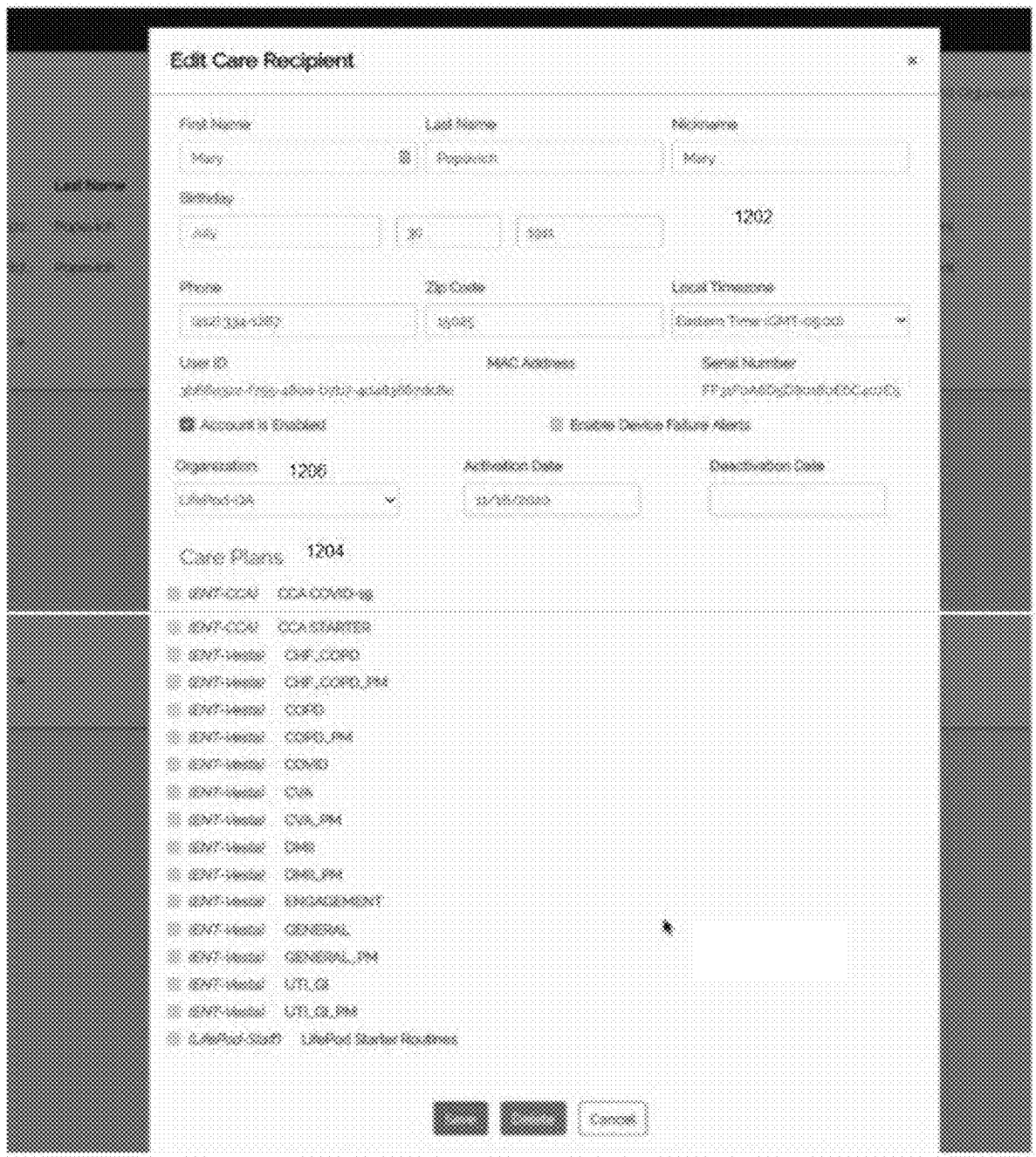
FIG. 12 is an example screen capture of the user interface for editing information associated with the care recipient, according to one embodiment.

Shown in FIG. 12 is an example screen capture of the user interface for managing care plans on a user basis. Responsive to selection of a specific user on the system, user interface can transition to a user display "edit care recipient". For example, information on a specific user will appear in the upper portion of the display screen (e.g., at 1202). The user interface can include displays that enable organization assignment and/or display of information about assigned organizations (e.g., 1206). When an organization is selected (e.g., at 1206), the care plans associated with that organization will be shown in the bottom portion of the screen for example, at 1204. In some embodiments, the listing of care plans at 1204 can be system selected. For example, the system can include artificial intelligence to match the user, their demographics, their conditions, their age, similar users, etc. to routines that machine learning models determine would be beneficial or match conditions or diagnoses of the currently visualized user. In other embodiments, an organization can define display order for care plans that are likely to be used or needed by their members. In some examples, the organization defined display order can be established based on artificial intelligence analysis.

According to some embodiments, selections of care plans (e.g., COVID-19, starter, CHF_COPD, etc.) triggers the system to automatically schedule times associated with each individual routine referenced within the selected care plans. In various embodiments, the system is configured to select timing, scheduling, and/or ordering based on any one or more of the following: organization rules, priority definition, priority category, among other options.

Figure 13:
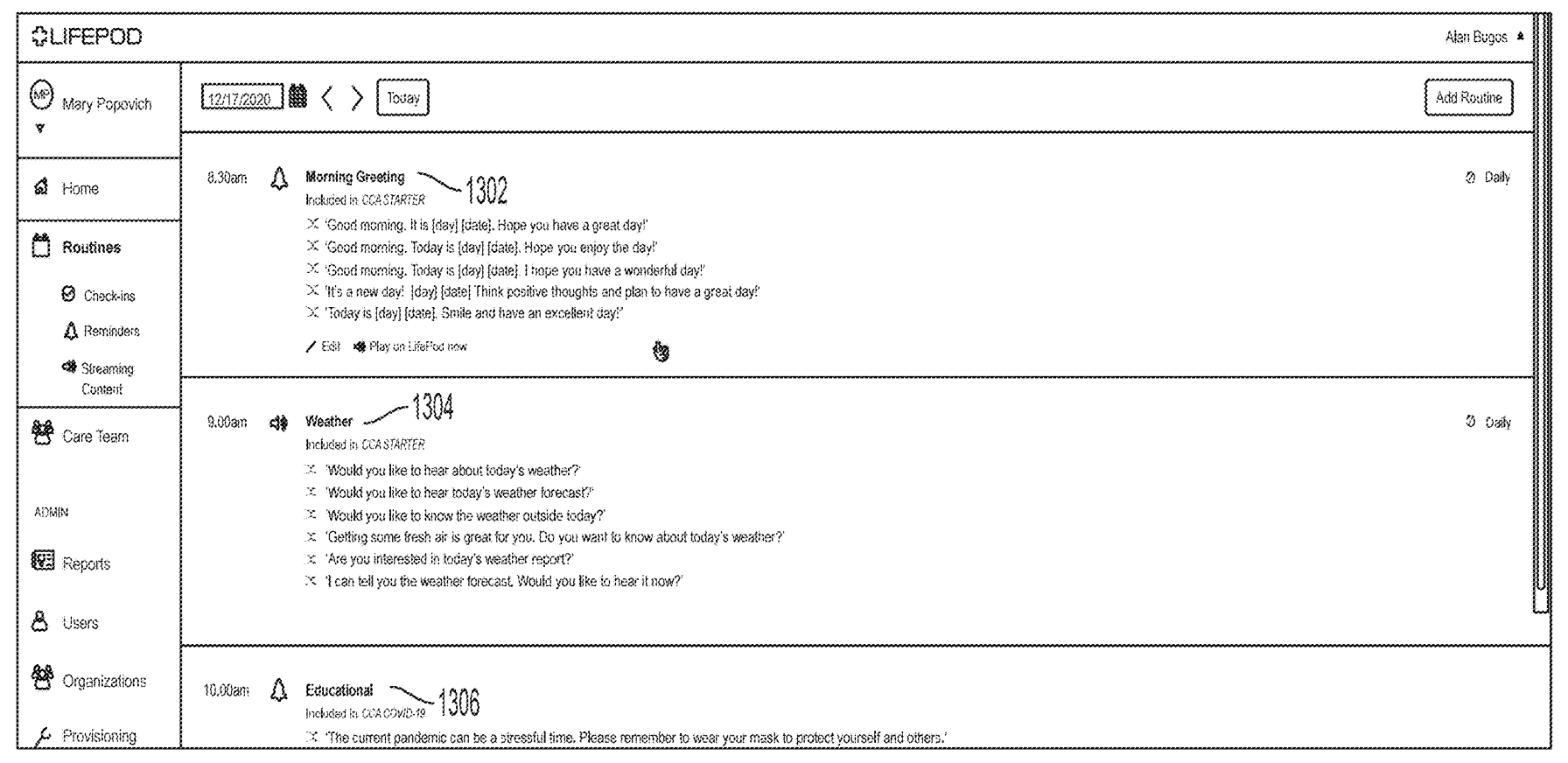

FIG. 13 is an example screen capture of the user interface showing a detailed view of the signed user routines. In FIG. 13 shown is a first routine to be executed as a morning greeting at 1302. The morning greeting can include any number of introductions and request for confirmation from user. The routine can be established with multiple greeting messages where only one will be played as a given execution. The routine is configured to select a greeting message randomly from a group of predefined greetings. In further example, a routine can be based on a permissive prompt—"would you like to . . . ". A list of permissive requests can be used to provide variety, by having the system randomly select from the group of requests. Additional routines will display on the user interface (e.g., 1306) and be selectable by scrolling through the user interface.

Figure 14:
FIG. 14 is an example screen capture of a routine generation interface, according to one embodiment.

FIG. 14 is an example screen capture of a routine detail display. In some examples, the user can access the detail displaying to customize settings for the particular routine (e.g., change date and time, recurrence, follow-up status, etc.). In some embodiments, the detail screen can include a display detailing that the routine is part of a routine package or care plan (e.g., at 1402).

FIG. 15 is an example screen capture of an add routine user interface. Pre-existing routines can be accessed in the interface and configured for a user with a few clicks in the UI. In various embodiments, the system is configured to organize routines or care plans to facilitate configuration for a particular user. In one example, routines can be organized based on a type (e.g., wellness checking, social reminder, content, etc.). Shown at 1502 is an option to select common and/or popular routines for a user. In one example, daily exercises display is shown at 1502, hydration at 1504, medication at 1506, morning check in at 1508, among other options. These routines can be presented by default and/or based on an organization's settings. In other examples machine learning algorithms can identify these routines as the most likely to be useful for a particular user. Similarly, shown it 1510 is a caregiver visit reminder, at 1512 a favorite TV show reminder, at 1514 a religious service reminder, at 1515 an upcoming birthday reminder, at 1516 a listen to music routine, at 1518 a news briefing routine and at 1520, a today's weather routine. In other embodiments, different routines can be displayed, and/or different routine ordering may be presented depending on the characteristics of the user, the entity they are associated with, intelligent algorithms, among other options.

Figure 16:
FIGS. 16-17 are example screen capture of a routine generation interface, according to one embodiment.

FIG. 16 is an example screen capture of the user interface to add a wellness check that is a hydration routine. When adding the routine for execution a date and time can be assigned as well as details for any repetition. As shown in the user interface specific voice prompts can be assigned and/or tailored to the user in question. As an example, default setting, the routine may include an initial question, a reply if the answer is yes or positive, a reply if the answer is no or negative, among other options. In some examples, custom voice models may be tailored to a specific user by the system. In one example, machine learning algorithms are trained on a user's responses to example voice prompts. Various machine learning models can be tailored to determine responsiveness to question types and/or format and use those determinations to customize a script associated with various voice prompts based on user characteristics.

Figure 17:

Shown in FIG. 17 is an example screen capture of a user interface for creating a routine. According to various embodiments, routine creation can generate conflicts between existing routines, custom routines, routine packages or care plans, among other options. In various embodiments, the system is configured to highlight any potential conflict for example at 1702 where the system displays a warning message of multiple routines scheduled at the same time. In one example, the system is configured to prevent a user from selecting the same time for multiple tasks or routines, and the user interface greys out times that have routines already selected. In another example, the system is configured to enable users to schedule routines for the same time and the system is configured to resolve scheduling conflicts automatically.

According to one embodiment, the system can implement an execution queue in order to manage execution of routines as they appear on the system at the same time (e.g., in order created, and a priority order, ordered by category, ordered by creator, among other options). According to some embodiments, system generated conflict resolution can in fact result in conflicts with subsequent routines. For example, pushing a routine's execution time back in order to resolve an initial conflict may in fact generate a new conflict with a subsequent routine. In some embodiments, the system executes conflict resolution on the secondary conflict which will result in one of the conflicting routines executing first and the remaining routine executing at a later time. Each delay in routine execution can result in subsequent conflicts, and each conflict will be resolved by the system automatically.

Care Management Entity and Example Environment

According to one embodiment, the voice assistance system can be configured to support a care management entity and its membership. Further descriptions and details are provided with respect to interactions between the care management entity and the system to illustrate various functions and not to limit the scope of the invention. For example, in the care management setting various routines types can be specified.

Example routine definitions include: a care plan routine that is defined as a group of routines created by an administrative user (e.g., organization/entity admin, etc.) and is executed for all or some logical grouping (e.g., departments, cohorts, business units, etc.) of an organization; a private routine that is defined as an individual routine created by a caregiver (e.g., a family member or medical staff caring for the care recipient, etc.) based on the care recipient's needs or by the care recipient; an emergency routine that is defined as a routine created by the system either via AI logic or via explicit logic by a rules engine to resolve emergency issues (e.g., fall, ambulance, trigger EMS, negative response threshold met, emergency word response, event of concern, etc.); a transportation routine that is defined as a reminder routine, including, just in time transportation routine reminders for the care recipient that can be generated by a third-party system (e.g., via API) which may hold the transportation data for the care recipient and/or service the request; and a critical routine that is defined as any routine (e.g., any kind of routine mentioned above) where care recipient responses need timely attention (e.g., by the caregiving team), which can include, for example, routines given a critical status by a privileged user, and various routines reflecting medically necessary care, among other options. In various embodiments, the different routine types can further include information on how the routine is created (e.g., by a voice device user (e.g., the care member), by the system, by the entity, by a third-party interface, among other options)).

In various embodiments, the system is configured to support any one or more and any combination of the following settings: a care plan routine (e.g., group or set of routines) can be customized for a care member or care recipient; a care partner (e.g., a user with authority to manage the routines and monitor the responses of care recipients) for a care member can create a personalized routine; a personalized routine can be created within certain boundaries or guidelines and may not be completely designed nor tested as per system designed routines; a third-party system can generate a personalized routine (e.g., a transportation reminder for that care member's doctor appointment) for a care member. In one embodiment, the voice assistance system includes API to interact with transportation services and generate custom routines for members automatically. For example, the system can interface with the known Coordinated Transportation Solution organization, to accept information on scheduled transportation services, among other options (e.g., UBER, LYFT, etc.). In one example, the transportation API is configured to generate a member specific proactive routine for a transportation reminder before a set time period (e.g., 5, 10, 15, 20, 25, . . . , minutes before) of a doctor appointment or other transportation request.

As discussed above, the system can be configured to set an individual care plan routine schedule for a care recipient and to disable some care plan routines for a care recipient as part of routine assignment, creation, management, and/or customization. In some embodiments, the system is configured to enable: customization/creation of a care plan routine for a care member; customization by the care member, caregiver, care management entity, and/or automatically by the system (e.g., via third-party systems or AI identified routines/routine customization).

In some embodiments, the system is configured to manage existing routines to facilitate customization. For example, routine can include a number field to define what actions are executed and when. The following fields can be defined for a given routine and the respective fields are enabled for customization: recurrence timing, recurrence type, execution timing (e.g., start, stop, before, after, etc.), etc. Some further examples include the following individual fields: recur_monthly_on_day, recur_once_on_date, recur_weekly_on_Friday, recur_weekly_on_Monday, recur_weekly_on_Saturday, recur_weekly_on_Sunday, recur_weekly_on_Thursday, recur_weekly_on_Tuesday, recur_weekly_on_Wednesday, recur_yearly_on_day, recur_yearly_on_month, recurrence_type, run_at_hour, run_at_minute, start_date, etc.

In some embodiments, the system employs a database or table for a user that specifies when an existing routine has been customized (e.g., custom: true/false, 0/1, etc.). Table I specifies fields, data type, value, and a description of the field in the notes column for each name record from column name.

TABLE I

| Column Name | Data Type | NULL | Notes |
| --- | --- | --- | --- |
| id | UUID | NO | Primary key |
| date_created | timestamp | No | Record create Date/Time |
| created_by | UUID | Yes | uuid of app_user created the record |
| date_modified | timestamp | No | Record update Date/Time; can include log of past modification dates |
| modified_by | UUID | Yes | uuid of app_user modified the record |
| version | int4 | No | Version number |
| app_user_id | UUID | No | UUID of care recipient |
| routine_id | UUID | No | UUID of care plan routine |
| run_at_hour | int4 | yes | |
| run_at_minute | int4 | yes | |
| recurrence_type | int4 | yes | |
| recur_monthly_on_day | int4 | yes | |
| is_enabled | bool | yes | True (default)/False: System can control play - setting this field to False routine does not play on a member's device |
| start_date | date | yes | |

According to one aspect, enabling customization and/or routine creation can lead to conflicts in timing, execution, scheduling, etc. In some embodiments, routines can be given priority values, that can be used by the system to resolve any conflict and/or to avoid any conflict in the first instance. According to one embodiment, a routine may be assigned priority based in routine type, which include, for example, care plan routine, private routine, transportation routine, emergency routine etc. Other examples, any of which may be used alone or in combination include: emergency, transportation, private, care plan routine, among other options.

According to further embodiments, the system is configured to assign a priority level for each defined routine type, with priority levels being exclusive. In this context priority exclusivity is used to defined priorities so that no two routine types can have the same priority level. One example for priority assignment includes: (1) emergency, (2) transportation, (3) private, (4) care plan routine, where the ordering 1-4 establishes which priority type is executed and/or scheduled first on the system where a conflict is present. In various embodiments, the priority levels and priority level designations are configurable by a privileged user. According to some embodiments, different priority levels can be used on the system and different orderings may be assigned. In one example, routines with external dependencies (e.g., dependent on external systems for execution or management (e.g., a transportation request)) can all be treated under the transportation priority or be given an external dependency priority that is executed by the system after emergency but before other priority types.

Where the system encounters routines scheduled for the same time slots, the system can be configured to queue the routines and execute them according to their respective priority level value specified for the routine type. For example, if an emergency routine and care plan routine are scheduled for 8:45 AM, then the system is configured to execute the emergency routine first (since this routine type has the highest priority level) after that the care plan routine is executed. In another example, if two "private routines" are scheduled for 8:45 AM, then the system can be configured to treat them equally (e.g., no priority—played one after another). Some other embodiments include additional priority values within each routine category. The system can be configured to use additional priority values to order execution within a routine category.

According to one embodiment, the system can include a natural language understanding engine (a "NLU engine") that is configured to determine an intent associated with each routine. The intent information can be used by the system to prioritize execution on the basis of most relevant intent for that time (e.g., same private routines at 8:45 AM—Routine 1—Please take your blood pressure meds=>medical treatment intent; Routine 2—Your favorite morning TV show is coming in 15 minutes=>reminder of upcoming event intent; Routine 1 will be prioritized because its intent is associated with a current action versus the reminder of a coming event). In some examples, the system can be configured to modify the dialog of the second routine based on how long of a delay is induced by executing Routine 1 first (e.g., 5 minutes to take medication and acknowledge, Routine 2 automatically modified for that instance to change the dialog to a 10 minute reminder). In some examples, routine intent can be used as an ordering framework to resolve execution ordering. In one embodiment, the system can include a machine learning model trained on prior orderings (e.g., based on priority) and an NLU intent. The machine learning model can automatically link various intents to orderings based on the prior execution orderings. The ML ordering can be used as a recommendation, default ordering, etc., and may require review and approval before implementation. For any intent the machine learning model cannot resolve, the exception can be automatically surfaced to privileged users for resolution.

In further embodiments, the system can be configured to manage routine execution based on intent. For example, any individual routine can be configured with an intent or an intent can be interpreted from the dialog of the routine and/or answers provide by the users in responses to questions asked during execution of the routine. In one example, the system can include a routine with a dialog that asks a medication question ("Did you take your medication"). The intent that can be assigned and/or inferred is to request medication status/compliance with a medication regime. In some examples, the system defines a "binding intent" for variable for such routines, "takenmeds." The variable is established with possible yes/no values. In further example, the system can execute a routine with a dialog option to ask a weather question ("Do you want to know todays' weather"). In some embodiments, the system can have defined a binding intent for a variable "interestedinweather." In further example, the variable can be defined to include possible yes/no value, etc. Other examples can include intent variables with multiple possible values (e.g., and answer values can also be linked with intent information).

According to some embodiments, the system can be configured to prioritize routine execution based on prioritization of intent that are linked to a routine and/or inferred from user responses. For example, priority ordering on intent can be applied to intents that fall within the following ordered categories:

1. 3rd party system routine/reminder (e.g., just in time transportation arrival reminder);
2. Medical action (e.g., "takenmeds" intent);
3. Healthy habits (e.g., drinking water, stretching, etc.);
4. Social action/activity (e.g., watch TV show, play cards, etc.);
5. General reminder
6. Birthday reminder
7. Caregiver arrival Other embodiments can include different orders of priority. In further embodiments, the device user and/or privileged user can adjust intent-based ordering, and for example, have those preferences stored in a user profile.

According to one embodiment, the system can include and employ a "critical" setting for various routines. In one example, the critical setting can be configured to override other priority settings. In another example, where a critical routine (e.g., is_critical=true) value has been set, that routine is configured to play first. An example includes an emergency and care plan routines that are scheduled for 8:45 AM, where the care plan routine is critical, this results in the system executing the care plan routine first and after that the emergency routine. Another example includes an emergency and care plan routine that are scheduled for 8:45 AM, where the care plan routine is critical and emergency routine is critical, then the emergency routine is executed played first (since this routine type has the highest priority level) and after that the care plan routine. In some embodiments, the system can use execution delays to resolve conflicts. For example, the system can evaluate priority and delay execution on a task with a lower priority (e.g., 5 minutes, 10 minutes 15 minutes, etc.).

In some embodiments, system and/or user interface are configured to display a warning message for routines (e.g., private, etc.) created through the portal when the system determines there is overlap with another routine. In other embodiments, the system and/or user interface can prevent scheduling overlap by greying out or preventing selection of an overlapping time in the user interface. In one example, if a caregiver schedules a routine for 8:45 AM and there is a care plan routine scheduled for the same time, then the system is configured to warn the caregiver—"There are other routines scheduled for the same time, there might be 2-3 minutes delays. Would you like to select a different time slot?" In further example, the caregiver can prioritize the routine (e.g., set is_critical flag), which can alter execution order as described above.

According to some embodiments, the system can be configured to manage task execution on a time period basis (e.g., a day, twelve hour window, week, etc.). In one example, a task schedule is configured to populate a routine table daily for the next 24 hours. This functionality can be implemented to limit requests for routine data from a routine database multiple times throughout a given day. An example sequence of execution includes: a task scheduler process populates routine_scheduled table daily for the next 24 hours, (polling for delayed tasks stage) checks for routines that should be executed now where data is loaded to in-memory storage Redis Key value store, (Polling for Tasks Execution stage) polling from separate queues→routines are queued in Redis pub sub respective of the priorities assigned, (AVS Subscription handler stage) reads the data from Redis pub sub, generates routine_execition_id, sends routines to devices and offloads routine execution data to TimeseriesDB routine_execution_data_table, and (AVS Subscription handler stage) writes routine execution data to TimeseriesDB routine_execution_results table.

In further embodiments, the system is configured to enable routines from different care plans to be set for the same time. For example, the system is configured with settings allowing prioritization of care plans (e.g., routine packages) that delays lower priority care plan routine(s) while routine from a care plan with a higher priority is played first. In one example, if we have an overlap of a basic care plan routine with a routine from a "COVID-19" care plan, then based on priority of the care plan assigned the routine from COVID-19 care plan is played first, after that the basic care plan. In some settings, machine learning analysis can be used to evaluate care plans and assign relative priority to respective plans. In other embodiments, category information can be used to assign a default priority to care plans.

Conflict Avoidance Examples

Various settings and/or architectures enable the system to evaluate customization requests and resolve specific conflicts, including those based on need or necessity. In a health care setting, the system can recognize a request to terminate routines for medically necessary functions (e.g., medication) and reject or reformat such customizations. In the alternative and/or in another embodiment, the system can determine a baseline or default function has been replaced by a customized function, and the system can permit de-activation of pre-configured "necessary" routines in favor of a customized user routine. In other embodiments, the system is architected to minimize conflict space in generation and/or management of default or group-based routines or functions. Not only are various embodiments configured to ensure medically necessary functions are executed, but the system can also be configured to avoid conflicts that result from user customization. In some examples, time division functions are used to avoid conflict, and in others locking mechanisms can be used to avoid conflicts.

For example, routines can be created and/or defined on the system that specific action to be taken on a user device, where each action (e.g., voice input request, confirmation request, assistance action, analysis, communication, etc.) can be associated with a duration for execution. In addition to maintaining durations associated with individual actions, groups or sequences of actions, the system is configured to manage time assignments to respective actions. Time slices can be selected and/or reserved to minimize or avoid conflict with customization of respective actions by the user. In one embodiment, the system is configured to implement time slices associated with a specific duration (e.g., the specific duration can be tailored to selected actions, or be assigned by the system based on group of actions to be configured (e.g., shortest action duration can be assigned to duration of the time slice, average duration, longest durations, multiple of shortest and/or longest, among other options)).

Figure 18:
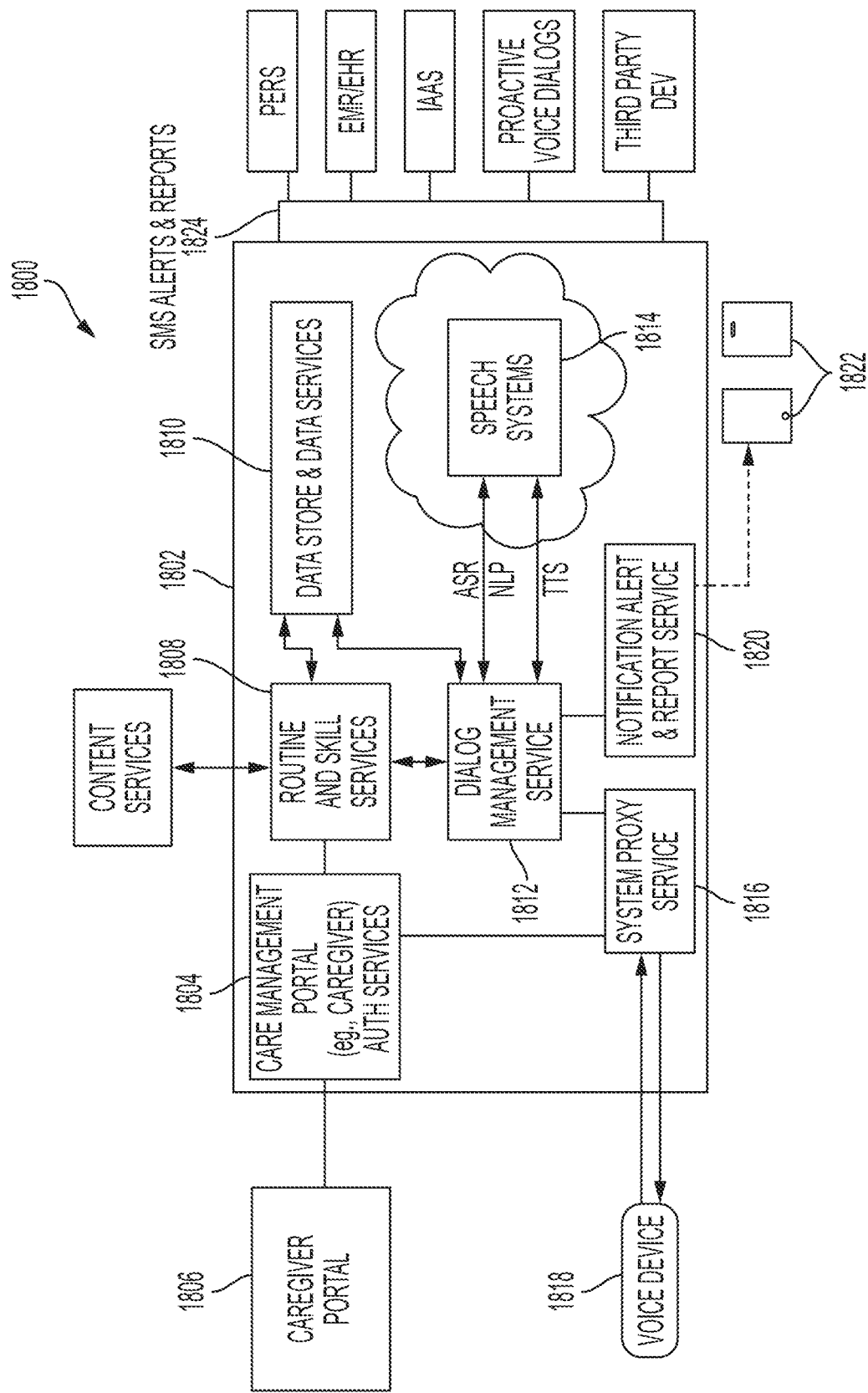
FIG. 18 is a block diagram of a voice assistance system, according to one embodiment.

Shown in FIG. 18 is a block diagram of an example system 1800 that supports a care service provider, caregivers, and care recipient members. According to one embodiment, the system can include a care platform 1802 configured to manage care services and interactions with the caregiver portal to deliver voice routines to user devices. At 1804, a care management or administration portal is configured to authenticate access to the care platform and/or a caregiver portal (e.g., 1806). The care management portal is configured to provide routine and skill services administration functions and may interact with a routine and skills services component 1808 to deliver and manage sets of skills, routine packages, individual routines, etc., assigned to users (e.g., care recipients). The settings defined by the care management portal and or the routine and skill service component can be stored in respective data stores and data services, at 1810. This can include information on an associated care service provider, default routines established by the provider, custom settings, routine packages, among other options. Additionally, the data store 1810 can include various databases where each database is configured to host targeted information. For example, the system can include a database configured to hold information on assigned routines, care packages, and/or customizations (e.g., timing, recurrence, etc.) on those routines. In another example, the system can include a database configured to store information on care recipient activities executed via the voice device, and can also include information on interactions with the voice device (e.g., voice responses, negative responses positive responses, failed responses, emergency requests, environment information, etc.). The data store can also include demographic information on device user populations and build profiles on users, customizations, and utilization of voice assistance services.

Various embodiments of the care platform can perform any of the functions described above with respect to voice assistance and/or voice assistance actions. For example, caregivers can interact with the platform via caregiver portal 1806 and perform any of the functions discussed herein with respect to caregivers. Once routines have been defined, a dialogue management service 1812 can assist in execution of various routines. For example, routines are typically associated with a voice dialogue and the dialogue management service can capture text-based dialogue and translate the text-based dialogue into verbal requests and/or instructions. In one embodiment, the dialog management service 1812 is configured to interact with speech systems available online. According to one embodiment, speech systems 1814 can provide natural language processing ("NLP") functions as well as automatic speech recognition ("ASR") functions, as well as text to speech functions ("TTS"), among other options.

According to some embodiments, the care portal is configured to manage operations for hundreds and/or thousands of user voice devices. According to one embodiment, the care platform can include a proxy service 1816 to facilitate management of routine execution, dialogue, and/or verbal response interpretation. In some examples, the proxy service 1816 can be configured to implement execution queues that can be associated with users via a unique user ID. According to one embodiment, the dialogue management service 1812 and proxy service 1816 can operate together to generate schedules for execution of assigned routines. In one example the system can also include a task schedule plus and operating delay to ensure that tasks are queued and executed according to the schedule while giving time for task preparation, distribution, and execution among other options. In some embodiments, a routine schedule is developed and sent to a Redis store for execution of ready tasks. Redis is a known implementation of an in-memory-key-value database, cache, and message broker. Other in-memory databases can be configured to handle queued execution of routines in connection with a dialog manager and respective voice devices. In further embodiments, the ready tasks can be polled and executed based on priority assignment. Once ordered by priority, any scheduled routines for a time period can be executed.

According to some embodiments, various voice devices (e.g., 1818) can include voice service applications. For example, a voice device 1818 can include the known AVS—Alexa voice services. In various embodiments the proxy service 1816 can interact with voice services on the user device 1818 to deliver both proactive voice control and reactive voice control to accomplish routine execution and or content delivery, among other options.

In further embodiments the dialogue management service 1812, can also be configured to generate and deliver notifications, alerts, and the reports to various user devices. In one example SMS alerts and reports can be delivered to caregivers via registered devices. In other embodiments, care recipients can register their own user devices and define routines for triggering notifications and/or alerts to their own devices.

According to various embodiments, the platform can include a middleware layer 1824 configured to interact with various external systems and/or services for example, the platform can connect to personal emergency response services, and users can trigger PERS based services the invoice imports to their voice device (e.g., 1818). The plan for middleware 1824 can be further configured to manage operations and/or connections to EMR/EHS services, infrastructure as a service systems, proactive voice dialogues, third-party development systems (e.g., digital/CMS) shown at 1850, among other options. In other embodiments, the platform middleware can be configured to connect and interact with a variety of other services and/or platforms. In some settings, the platform and middleware can be configured to access and employ third-party services via various voice prompts delivered and/or requested from user voice devices (e.g., 1818). In some examples, the platform can turn any online service into a voice assistance or voice interactive service. In some embodiments, content and services 1830 can also be integrated through routine and skills execution.

Machine Learning Examples

According to various embodiments, the system can employ various machine learning models to optimize routine selection, routine execution, routine scheduling, and/or routine customization, among other options. For example, the system can collect information on users and their voice devices, as well as information pertaining to routine execution compliance/anomalies and any associated customizations made that result in an improved execution percentage or a reduced execution percentage or other issues. According to one embodiment, user demographics are modeled in conjunction with routine execution information (e.g., compliance, completion, encountered issues, etc.) to filter user groups and identify characteristics that are likely to improve routine execution.

In other embodiments, the system can use machine learning models to determine routine customizations that may be used to improve routine execution compliance. For example, users with customizations can be analyzed to determine what customizations, if any, contribute to improved execution rates over, for example, a baseline population. Such customizations can be surfaced to administrative users for incorporation into routine packages. Alternatively, customizations that improve operation for a subset of users may be identified by the machine learning models, and those customizations require at least a similarity match to other users to improve routine execution compliance. In some examples, multiple machine learning models are used, one for similarity, one for customization identification, and the combination can yield recommendations for customizations for specific users and/or user groups. In some examples, classification models can be trained on user characteristics and routine behavior and other models can be used to identify customizations likely to improve routine execution compliance. In one example, an outlier identification model can be used to identify interesting customizations and still further models used to link interesting customizations to a likelihood of improving routine execution compliance.

In other embodiments, machine learning models (e.g., outlier detection models, classification models, etc.) can be used to identify customizations made by users at their respective devices that are linked to improvements on the system (e.g., efficiency, scheduling, compliance, and/or user satisfaction, among other options). The system can use these identifications build proactive routines that ask other users if they would like to implement the same customization to their activities. In some embodiments, the system can present customization options identified by machine learning models to various end users. The system can also be configured to build routines to verify satisfaction and/or present options to reverse the customizations. For example, the system can build a routine with a verbal request to a user—"do you want to return to your old schedule?"—that can be executed periodically, on a scheduled, or aperiodically after a recommended customization is made.

Various model types (e.g., classification models, regression models, outlier detection models etc.) can be implemented by the system to learn and train on user data captured during interactions with the user voice devices, and can also be based on demographic information made available on the system. The output of the various machine learning models can be used to surface recommendations to administrative users, surface recommendations to users of the voice devices, and/or to alter display ordering or highlight options identified by the machine learning analysis. In other embodiments, the system can be configured to automatically implement changes identified by the machine learning algorithms and monitor such changes to confirm or validate improved operation. In some examples, the system will create routines to reverse or rollback any automatic changes responsive to voice input of the user of the respective voice device. In further examples, the system can automatically rollback customizations that do not result in improved operation (e.g., based on the results of the monitoring).

Figure 19:
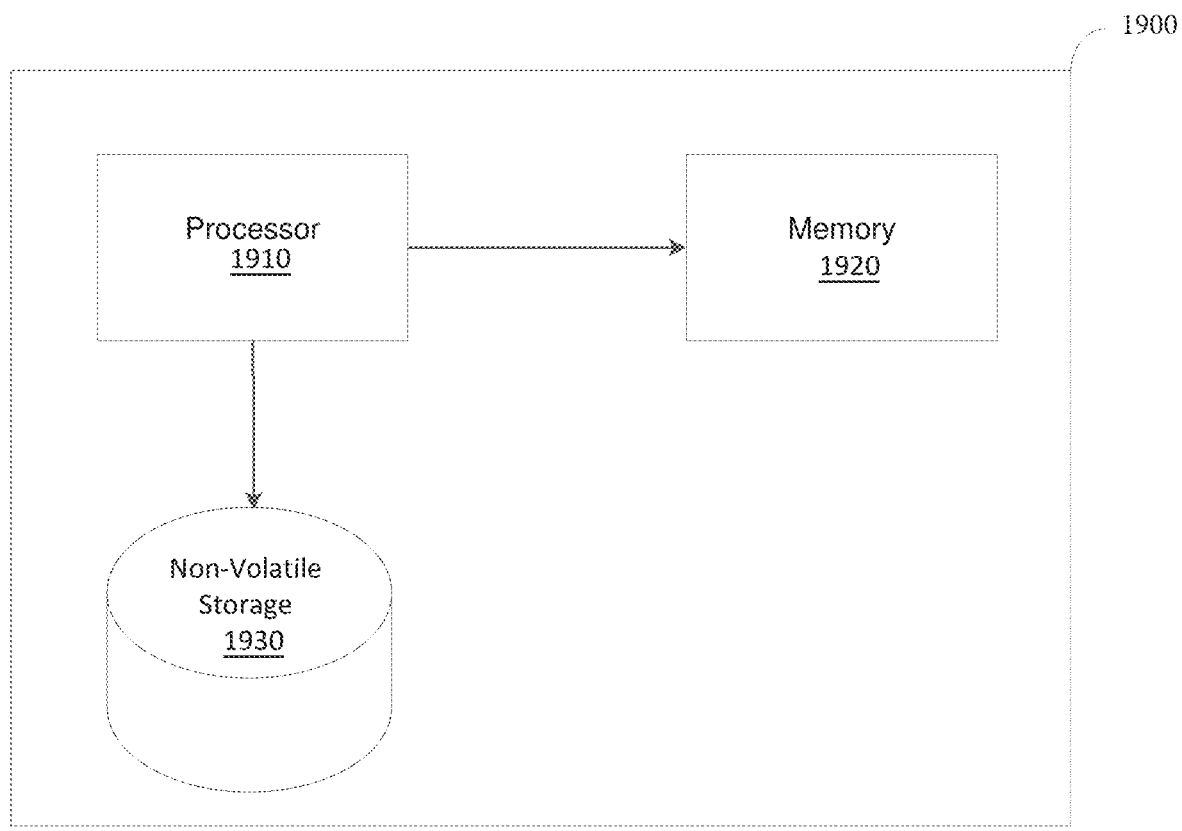
FIG. 19 is a block diagram of a special-purpose computer system capable of executing the functions described herein.

An illustrative implementation of a computer system 1900 that may be used in connection with any of the embodiments of the disclosure provided herein is shown in FIG. 19. The computer system 1900 may include one or more processors 1910 and one or more articles of manufacture that comprise non-transitory computer-readable storage media (e.g., memory 1920 and one or more non-volatile storage media 1930). The processor 1910 may control writing data to and reading data from the memory 1920 and the non-volatile storage device 1930 in any suitable manner. To perform any of the functionality described herein, the processor 1910 may execute one or more processor-executable instructions stored in one or more non-transitory computer-readable storage media (e.g., the memory 1920), which may serve as non-transitory computer-readable storage media storing processor-executable instructions for execution by the processor 1910.

The terms "program" or "software" are used herein in a generic sense to refer to any type of computer code or set of processor-executable instructions that can be employed to program a computer or other processor to implement various aspects of embodiments as discussed above. Additionally, it should be appreciated that according to one aspect, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc., that perform particular tasks or implement particular abstract data types. Typically, the functionality of the program modules may be combined or distributed as desired in various embodiments.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Also, various inventive concepts may be embodied as one or more processes, of which examples have been provided. The acts performed as part of each process may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, and/or ordinary meanings of the defined terms. As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items. Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

The invention claimed is:

1. A voice assistance system for managing voice routine execution in a user environment, the system comprising:
    at least one processor operatively connected to a memory;
    at least one server system;
    a plurality of voice devices, the plurality of voice devices comprising at least a speaker for communicating voice commands and a microphone for receiving voice input, wherein the plurality of voice devices are configured to enable assistance actions for respective users of the voice devices based on execution of voice routines;
    wherein the at least one processor is configured to:
        manage execution of a plurality of voice routines, the plurality of voice routines having associated execution times or triggers and an associated duration;
        store a user profile for the respective user of the voice device specifying one or more voice routines associated with a respective voice device, wherein the user profile defines the associated execution time or trigger of the one more voice routines in the user profile;
        identify overlapping execution of a plurality of voice routines for respective users based on any one or more of the associated execution time or trigger, any customization of timing or trigger, or the associated duration for the plurality of voice routines;
        generate an ordering of execution for the plurality of voice routines for a respective user; and
        manage execution of the plurality of voice routines at the respective user's voice device according to the generated ordering.

2. The system of claim 1, wherein the at least one processor is configured to execute operations at respective voice devices, the server, and/or additional distributed computer resources.

3. The system of claim 1, wherein the at least one processor is configured to:
    generate an execution queue for the plurality of voice routines.

4. The system of claim 3, wherein the at least one processor is configured to resolve any overlapping execution based on priority assignment or determination associated with the plurality of voice routines.

5. The system of claim 3, wherein the at least one processor is configured to populate a first in first out queue based on the generated ordering of the execution.

6. The system of claim 5, wherein the at least one processor is configured to generate the ordering of the execution to include a secondary ordering within respective priority assignment or determination.

7. The system of claim 6, wherein the at least one processor is configured to populate a first in first out execution queue based on the secondary ordering.

8. The system of claim 1, wherein the at least one processor is configured to communicate voice routines for a set time period or trigger to a database, and the database is configured to manage ordering operations on the voice routines and distribution of the voice routines to respective user devices.

9. The system of claim 1, further comprising voice routine application programming interfaces (APIs) configured to accept external generation of voice routines for execution at the plurality of user devices.

10. The system of claim 9, wherein the at least one processor is configured to assign an execution priority to the voice routines generated via external systems based on at least one of a respective external system source for the voice routine, an action specified for the voice routine, or a category assigned to the voice routine.

11. The system of claim 1, wherein the at least one processor is configured to automatically customize an execution time or trigger of at least one voice routine in a group of voice routines having overlapping execution times or triggers, or durations.

12. The system of claim 1, further comprising a voice routine generation interface, wherein the voice routine generation interface is configured to prevent selection of overlapping timing of execution.

13. The system of claim 1, wherein the at least one processor is further configured to:
    identify a currently executing voice routine conflicts with an upcoming voice routine; and
    resolve the conflict based on ordering execution, delaying the upcoming voice routine, or rescheduling the upcoming voice routine.

14. A computer implemented method for managing voice routine execution in a user environment, the method comprising:
    registering, by at least one processor, a plurality of voice devices, the plurality of voice devices comprising at least a speaker for communicating voice commands and a microphone for receiving voice input, wherein the plurality of voice devices are configured to enable assistance actions for respective users of the voice devices based on execution of voice routines;
    managing, by the at least one processor, execution of a plurality of voice routines, the plurality of voice routines having associated execution times or triggers and an associated duration;
    storing, by the at least one processor, a user profile for the respective user of the voice device specifying one or more voice routines associated with a respective voice device, wherein the user profile defines the associated execution time or trigger of the one more voice routines in the user profile;

identifying, by the at least one processor, overlapping execution of a plurality of voice routines for respective users based on any one or more of the associated execution time or trigger, any customization of timing or trigger, or the associated duration for the plurality of voice routines;

generating, by the at least one processor, an ordering of execution for the plurality of voice routines for the respective user; and managing, by the at least one processor, execution of the plurality of voice routines at the respective user's voice device according to the generated ordering.

15. The method of claim 14, wherein the method further comprises executing operations at respective voice devices, the server, or additional distributed computer resources.

16. The method of claim 14, wherein the method further comprises generating an execution queue for the plurality of voice routines.

17. The method of claim 16, wherein the method further comprises populating a first in first out queue based on the generated ordering of the execution.

18. The method of claim 16, wherein the method further comprises resolving overlap in the ordering of the execution based on priority assignment or determination associated with the plurality of voice routines.

19. The method of claim 18, wherein the method further comprises generating the ordering of the execution to include a secondary ordering within respective priority assignment or determination.

20. The method of claim 18, wherein the method further comprises populating a first in first out execution queue with the plurality of voice routines based on the secondary ordering.

* * * * *